US008206685B2

(12) United States Patent
Chakrabarty et al.

(10) Patent No.: US 8,206,685 B2
(45) Date of Patent: Jun. 26, 2012

(54) CUPREDOXIN DERIVED TRANSPORT AGENTS AND METHODS OF USE THEREOF

(75) Inventors: Ananda Chakrabarty, Villa Park, IL (US); Tapas Das Gupta, River Forest, IL (US); Tohru Yamada, Oak Park, IL (US); Arsenio Fialho, Lisbon (PT)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

(21) Appl. No.: 12/754,197

(22) Filed: Apr. 5, 2010

(65) Prior Publication Data
US 2010/0209355 A1 Aug. 19, 2010

Related U.S. Application Data

(63) Continuation of application No. 11/244,105, filed on Oct. 6, 2005, now Pat. No. 7,691,383.

(60) Provisional application No. 60/700,297, filed on Jul. 19, 2005, provisional application No. 60/680,500, filed on May 13, 2005, provisional application No. 60/616,782, filed on Oct. 7, 2004.

(51) Int. Cl.
*A61K 49/00* (2006.01)
*A61K 39/02* (2006.01)
*C07H 21/04* (2006.01)

(52) U.S. Cl. .... 424/9.2; 424/9.1; 424/184.1; 424/185.1; 424/190.1; 424/192.1; 424/234.1; 424/250.1; 424/253.1; 424/260.1; 530/300; 530/350; 536/23.1; 536/23.7

(58) Field of Classification Search .................. 424/9.1, 424/9.2, 184.1, 185.1, 190.1, 192.1, 234.1, 424/250.1, 253.1, 260.1; 530/300, 350; 536/23.1, 536/23.7
See application file for complete search history.

(56) References Cited

U.S. PATENT DOCUMENTS

| 5,681,810 | A | 10/1997 | Villemez et al. |
| 5,972,899 | A | 10/1999 | Zychlinsky et al. |
| 7,338,766 | B2 | 3/2008 | Chakrabarty et al. |
| 2002/0110872 | A1 | 8/2002 | Chakrabarty et al. |
| 2005/0037341 | A1 | 2/2005 | Dierynck et al. |

FOREIGN PATENT DOCUMENTS

| WO | 20004046177 A2 | 6/2004 |
| WO | 2005018662 A1 | 3/2005 |
| WO | 2006088580 A2 | 8/2006 |

OTHER PUBLICATIONS

Derwent Publication Ltd London, GB; Jun. 23, 2004, Ku R. et al., "Azurin as bacterial protein, with wide spectrum antitumor function and its use and medical composition" XP002499408.
Hong CS et al., "Disrupting the entry barrier and attaching brain tumors: the role of the Neisseria H.8 epitope and the Laz protein", vol. 5, No. 15, (2006) pp. 1633-1641 XP002499239.
Hiraoka et at, PNAS 101: pp. 6427-6432 (2004).
Punj et al., Oncogene 23: pp. 2367-2378 (2004).
Ye et al., "Ai Zheng" 24: pp. 298-304 (2003).
Yang, et al., Pharmacol. Res. 52: pp. 412-421 (2005).
Yamada et al., Cell Cycle 3: pp. 1182-1187 (2004).
Yamada et al., Cell Cycle 3: pp. e69-e72 (2004).
Yamada et al., Cell Microbiol. 7: pp. 1418-1431 (2005).
Punj et al., J. Bacteriol. 185: pp. 3167-3178 (2003).
Chakraba Microhloi. 185: p. 2683 (2003).
Voes et al., Biochemistry, John Wiley & Sons, pp. 415-417, 932 and 933 (1990).
Zaborina et al., Molecular Microbiology 31:5, pp. 1333-1343 (1999).
Anonymous "Plastocyanin precursor" Database EMBL, Online Nov. 1, 1997, XP002306632 abstract.
Anonymous "Rusticyanin precursor" Database EMBL, Online Mar. 1, 1992, XP002306633 abstract.
Anonymous "Pseudoazurin precursor" Database EMBL, Online Feb. 1, 1991. XP002306634 abstract.
Confer et al., Am. J. Res. 53:5 pp. 646-652 (1992).
Wu et al., Antimicrobial Agents and Chemotherapy 44.5 pp. 1200-1297 (2000).
Kukimoto et al., FEBS letters 394: pp. 87-90 (1996).
Cutruzzola et al., J. Inorganic Chemistry 88: pp. 353-361 (2002).
Murphy et al., J. Mol. Biol. 315: pp. 859-871 (2002).
Punj et al., Cellular Microbiology 54:4 pp. 225-231 (2003).
Yamada et al., PNAS 99:22 pp. 14098-14103 (2002).
Coto et al , Mel. Vio, 47:2 pp. 549-559 (2003).
Punj et al., Biochemical and Biophysical Res. Comm. 32: pp. 109-114 (2003).
Zaborina et al., Infect. Immun. 67: pp. 5231-5242 (2007).
Melnikov et al., Microbiol. 36: pp. 1481-1493 (2000).
Punj et al., Infect. Immun. 68: pp. 4937-4937 (2000).
Zaborina et al., Microbiology 246: pp. 2521-2560 (2000).
Kim et al., The J. of Clinical Investigation, 105:7 pp. 837-839 (2000).
Sznol et al., The J. of Clinical Investigation, 105:8 pp. 1027-1030 (2000).
Pawelek et al., Cancer Research 57: pp. 4537-4544 (1997).
Potera, ASM News, 66:6 (2000).
Alexandroff et al., The Lancet, 53: pp. 1689-1694 (1999).
O'Donnell, Tibech, 15. pp. 512-517 (1997).
Paglia et al., Cancer Immunol. Immun. 46: pp. 88-92 (1998). Hunter et al., The J. of Immunology 166: pp. 5878-5881 (2001).
Dang et al., PNAS USA, 98: pp. 15155-15163 (2001).
R. K. Jain and N. S. Forbes, PNAS USA 98: pp. 14748-14750 (2001).
Vassaux et al., J. Pathology. 208: pp. 290-298 (2006).
Hummel et al J. Immunotherapy 28: pp. 467-479 (2005).
Anderson et al., J. of Molecular Biology 349:1 pp. 61-72 (2005).

*Primary Examiner* — Rodney P. Swartz
(74) *Attorney, Agent, or Firm* — Don J. Pelto, Esquire; Sheppard, Mullin, Richter & Hampton LLP

(57) ABSTRACT

The present invention discloses methods and materials for delivering a cargo compound into a cancer cell. Delivery of the cargo compound is accomplished by the use of protein transduction domains derived from cupredoxins. The invention further discloses methods for treating cancer and diagnosing cancer.

5 Claims, 11 Drawing Sheets wt azurin
14 kDa
SEQ ID No. 1    1 aecsvdiqgn dqmqfntnai tvdksckqft vnlshpgnlp knvmghnwvl staadmqgvv tdgmasgldk dylkpddsrv iahtkligsg ekdsvtfdvs klkegeqymf fctfpghsal mkgtltlk 128

1, GST 36-128 Azu 10
kDa+26 kDa
SEQ ID No. 5    GST- 36 pgnlp knvmghnwvl staadmqgvv tdgmasgldk dylkpddsrv iahtkligsg ekdsvtfdvs klkegeqymt fctfpghsal mkgtltlk 128

2, GST36-89 Azu 5.7
kDa+26 kDa
SEQ ID No. 6    GST- 36 pgnlp knvmghnwvl staadmqgvv tdgmasgldk dylkpddsrv iahtkligs 89

3, GST 36-77 sAzu
4.4 kDa+26 kDa
SEQ ID No. 7    GST- 36 pgnlp knvmghnwvl staadmqgvv tdgmasgldk dylkpdd 77

4, GST 36-50 sAzu
1.6 kDa+26 kDa
SEQ ID No. 8    GST- 36 pgnlp knvmghnwvl 50

5, GST 50-77 sAzu
2.9 kDa+26 kDa
SEQ ID No. 9    GST- 50 staadmqgvv tdgmasgldk dylkpdd 77

6, GST 50-68 sAzu
1.6 kDa+26 kDA
SEQ ID No. 10   GST- 50 staadmqgvv tdgmas 66

7, GST 67-77 sAzu
1.2 kDa+26 kDa
SEQ ID No. 11   GST- 50 gldk dylkpdd 77

8, GST
26 kDa

FIG. 2a

FIG. 3a
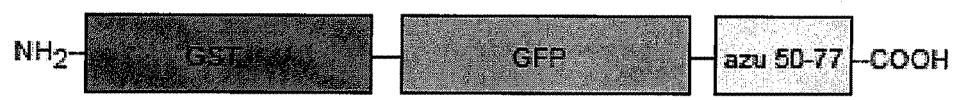
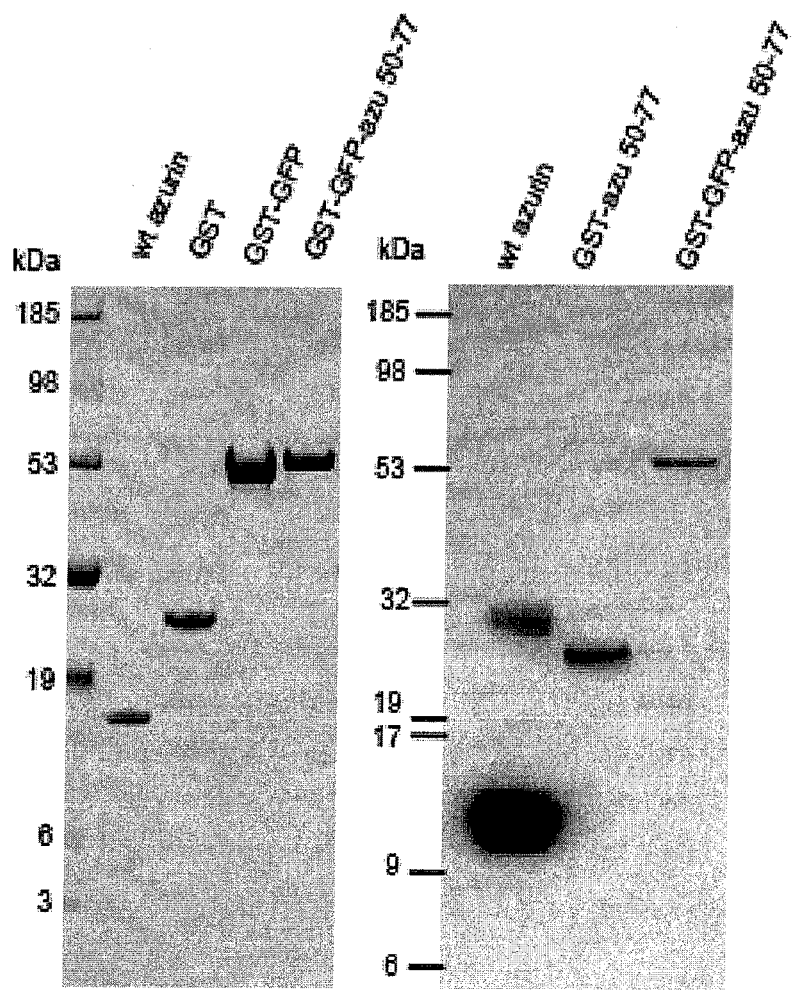
FIG. 3b  FIG. 3c

| Microorganism | Accession number | | | |
|---|---|---|---|---|
| Psae | AAG08307 | (51) | -STAADMQGVVTDGMASGLDKDYLKPDD | (77) |
| Pssy | AAO58351 | (51) | -SKKADASAITTDGMSVGIDKDYVKPDD | (77) |
| Neme | AAF41888 | (89) | IAKAEDMDGVFKDGVGA-ADTDYVKPDD | (115) |
| Vipa | NP_800938 | (52) | -ADTANIQAVGTDGMSAGADNSYVKPDD | (78) |
| Bobr | AZBR | (51) | -TKTADMQAVEKDGIAAGLDNQYLKAGD | (77) |
| Consensus | | | DG      D Y K D | |

US 8,206,685 B2

CUPREDOXIN DERIVED TRANSPORT AGENTS AND METHODS OF USE THEREOF

RELATED APPLICATIONS

This application is a Continuation and claims the benefit, under 35 U.S.C. §120, of U.S. Application Ser. No. 11/244,105 filed Oct. 6, 2005 now U.S. Pat. No. 7,691,383 which claims priority to U.S. Provisional Patent Application No. 60/616,782, filed Oct. 7, 2004, U.S. Provisional Patent Application No. 60/680,500, filed May 13, 2005, and U.S. Provisional Patent Application No. 60/700,297, filed Jul. 19, 2005. The entire content of those applications are fully incorporated herein by reference

BACKGROUND

The entry of a protein into a mammalian cell is often dictated by a small segment of the protein, which is commonly referred to as a "protein transduction domain" or PTD. This segment can be used as a signal attached to a foreign protein to facilitate transport of such a protein into a mammalian cell. For example, amphipathic peptides are used to facilitate uptake of DNA-cleaving metalloporphyrins as potential antitumor drugs in human fibroblasts HS68 or murine lymphocytic leukemia L1210 cells (Chaloin, L. et al. Bioconjugate Chem. 12:691-700, (2001)). Peptides, called cell-penetrating peptides, such as penetratin, transportan, Tat (amino acids 47-57 or 48-60) and the model amphipathic peptide MAP, have been used as delivery vehicles for transporting pharmacologically important substances, such as antisense oligonucleotides, proteins and peptides (Hallbrink, M. et al. Biochim. Biophys. Acta 1515:101-109 (2001); Lindgren, M., et al. Trends Pharmacol. Sci. 21:99-103 (2000)).

Such peptides, particularly the DNA-binding homeodomain of Antennapedia, a *Drosophila* transcription factor, or the 21 residue peptide carrier Pep-1, are internalized by many types of cells in culture, such as human HS68 or murine NIH-3T3 fibroblasts, at either 37° C. or 4° C. The lack of effect of the temperature shift suggests a penetration mechanism different from that of classical endocytosis (Morris, M. C. et al. Nature Biotechnol. 19:1173-1176 (2001)), which requires chiral receptor proteins. One of the most widely used peptides to transport pharmacologically-active compounds in mammalian cells is the eleven amino acid arginine-rich protein transduction domain (PTD) of the human immunodeficiency virus type 1 (HIV-1) transactivator protein Tat (Schwarze, S. R. et al. Science 285:1569-1572 (1999), Schwarze, S. R. et al. Trends Cell Biol. 10:290-295 (2000)). Intraperitoneal injection of the 120 kDa beta-galactosidase/Tat fusion protein results in the transcellular transduction of the fusion protein into virtually all tissues in mice, including the passage of the blood-brain barrier. This short peptide domain of HIV-1 Tat has been shown to mediate cell internalization of large molecules or particles, including magnetic nanoparticles, phage vectors, liposomes and plasmid DNA. Unlike the other cell-penetrating peptides discussed above, internalization of cargo proteins by full length Tat or its 11 amino acid transduction domain is significantly impaired at 4° C. (Liu, Y. et al. Nat. Med. 6:1380-1387 (2000), Suzuki, T. et al. J. Biol. Chem. 277:2437-2443 (2002)) and requires interactions with receptors such as the heparan sulfate chains of the cell membrane heparan sulfate proteoglycans.

Most of the PTDs identified to date have been derived from viral and mammalian sources. Other sources of PTDs would be desirable for the design of various experimental sequences, and for animal and human therapies and prophylactic procedures. One alternative source of PTDs is bacterial cells. Although bacterial proteins such as cholera toxin are known to enter mammalian cell cytosol (Sofer, A. and Futerman, A. H. J. Biol. Chem. 270:12117-12122 (1995)), the cytotoxicity of such proteins has limited the use of bacterial proteins, or PTDs derived from them, for transporting pharmacologically important cargos in mammalian cells.

SUMMARY OF THE INVENTION

One aspect of the present invention is peptide that has at least about 90% amino acid sequence identity to less than a full length wild-type cupredoxin or H.8 outer membrane protein, and which facilitates the entry of an linked cargo molecule into a mammalian cancer cell. In some embodiments, the peptide has at least about 90% amino acid sequence identity to less than a full length azurin, plastocyanin, rusticyanin, pseudoazurin, auracyanin or azurin-like protein, or to SEQ ID NO: 1, SEQ ID NO: 2, SEQ ID NO: 3, SEQ ID NO:4, SEQ ID NO: 29, SEQ ID NO: 30, SEQ ID NO: 31, SEQ ID NO: 32, SEQ ID NO: 33, SEQ ID NO: 34, SEQ ID NO: 36 and SEQ ID NO: 43. In some embodiments, the peptide is derived from *Pseudomonas aeruginosa, Phormidium laminosum, Thiobacillus ferrooxidans, Achromobacter cycloclastes, Pseudomonas syringa, Neisseria meningitidis, Vibrio parahaemolyticus, Bordetella bronchiseptica, Bordetella pertussis, Chloroflexus aurantiacus* and *Neisseria gonorrhoeae*. In other embodiments, the peptide is at least 10 residues and not more than 50 residues in length. In some embodiments, the peptide comprises a sequence which has at least about 90% amino acid sequence identity to SEQ ID NO: 5, SEQ ID NO: 6, SEQ ID NO: 7, SEQ ID NO: 9, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 46, SEQ ID NO: 47 or SEQ ID NO: 47. In other embodiments, the peptide comprises or consists of SEQ ID NO: 5, SEQ ID NO: 6, SEQ ID NO: 7, SEQ ID NO: 9, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 46, SEQ ID NO: 47 or SEQ ID NO: 47. In some embodiments, the peptide comprises the amino acid sequence DGXXXXXDXXYXKXXD (SEQ ID NO: 35) and DGXXXXDXXYXKXXD (SEQ ID NO:48), where D is aspartic acid, G is glycine, Y is tyrosine, K is lysine and X is any amino acid. Finally, in some embodiments, the peptide has significant structural homology to the 50-77 amino acid region of *Pseudomonas aeruginosa* azurin.

Another aspect of the invention is a complex comprising a cargo compound and an amino acid sequence, where the amino acid sequence has at least about 90% sequence identity with a cupredoxin, or a fragment thereof, the amino acid sequence, or fragment thereof, is linked to the cargo compound, and the amino acid sequence facilitates entry of the cargo compound into a mammalian cancer cell. In some embodiments, the amino acid sequence of this complex has at least about 90% amino acid sequence identity to less than a full length wild-type cupredoxin or H.8 outer membrane protein. In other embodiments, the cargo compound is protein, lipoprotein, polypeptide, peptide, polysaccharide, nucleic acid, dye, microparticle, nanoparticle, toxin or drug. In particular embodiments, the cargo is a protein or polypeptide which is linked amino acid sequence to form a fusion protein. In other particular embodiments, the cargo compound is a toxin, more particularly, the *Pseudomonas aeruginosa* exotoxin A. In other embodiments, the cargo is a detectable substance, more specifically one detectable by fluorimetry, microscopy, X-ray CT, MRI or ultrasound. Finally, the invention also encompasses the complex in a pharmaceutically suitable carrier.

Another aspect of the present invention is directed to a method for delivering a cargo compound into a cell. In one embodiment, this method comprises contacting a cell or cells with the above complex. In other embodiments, the cell or cells originate from a patient suffering from cancer, and are reintroduced into the patient. In other embodiments, the cell is a cancer cell, more specifically an osteosarcoma cell, lung carcinoma cell, colon carcinoma cell, lymphoma cell, leukemia cell, soft tissue sarcoma cell, breast carcinoma cell, liver carcinoma cell, bladder carcinoma cell or prostate carcinoma cell. In other embodiments, the complex is administered to a patient in a therapeutically effective amount. In other embodiments, the complex is administered intravenously, topically, subcutaneously, intramuscularly or into a tumor. In other embodiments, the complex is co-administered with another cancer treatment.

Another aspect of the invention is a method to diagnose cancer. In some embodiments, the complex with a cargo that is a detectable substance is administered to a patient with cancer and the location of the cargo is detected. In particular embodiments, the cargo compound is an X-ray contrast agent and is detected by X-ray CT, the cargo compound is a magnetic resonance imaging contrast agent and is detected by MRI, or the cargo is an ultrasound contrast agent and is detectable by ultrasound. In other embodiments, the cell or cells are contacted with a complex with a detectable substance and the location of the cargo is detected.

Another aspect of the invention is a kit that contains any of the above complexes. In some embodiments, the kit further comprises a pharmaceutically acceptable adjuvant or excipient. In other embodiments, the kit further comprises a vehicle for administration of the reagent.

BRIEF DESCRIPTION OF THE SEQUENCES

SEQ ID NO: 1 is the amino acid sequence of wt-azurin from *Pseudomonas aeruginosa*.

SEQ ID NO: 2 is the amino acid sequence of plastocyanin from *Phormidium laminosum*.

SEQ ID NO: 3 is the amino acid sequence of rusticyanin from *Thiobacillus ferrooxidans*.

SEQ ID NO: 4 is the amino acid sequence of pseudoazurin from *Achromobacter cycloclastes*.

SEQ ID NO: 5 is the amino acid sequence of the 36-128 amino acid fragment of wt-azurin from *Pseudomonas aeruginosa*.

SEQ ID NO: 6 is the amino acid sequence of the 36-89 amino acid fragment of wt-azurin from *Pseudomonas aeruginosa*.

SEQ ID NO: 7 is the amino acid sequence of the 36-77 amino acid fragment of wt-azurin from *Pseudomonas aeruginosa*.

SEQ ID NO: 8 is the amino acid sequence of the 36-50 amino acid fragment of wt-azurin from *Pseudomonas aeruginosa*.

SEQ ID NO: 9 is the amino acid sequence of the 50-77 amino acid fragment of wt-azurin from *Pseudomonas aeruginosa*.

SEQ ID NO: 10 is the amino acid sequence of the 50-66 amino acid fragment of wt-azurin from *Pseudomonas aeruginosa*.

SEQ ID NO: 11 is the amino acid sequence of the azu 67-77 amino acid fragment of wt-azurin from *Pseudomonas aeruginosa*.

SEQ ID NO: 12 is the amino acid sequence of the forward primer for pGST-azu 36-128.

SEQ ID NO: 13 is the amino acid sequence of the reverse primer for pGST-azu 36-128.

SEQ ID NO: 14 is the amino acid sequence of the forward primer for pGST-azu 36-50.

SEQ ID NO: 15 is the amino acid sequence of the reverse primer for pGST-azu 36-50.

SEQ ID NO: 16 is the amino acid sequence of the forward primer for pGST-azu 36-77.

SEQ ID NO: 17 is the amino acid sequence of the reverse primer for pGST-azu 36-77.

SEQ ID NO: 18 is the amino acid sequence of the forward primer for pGST-azu 36-89.

SEQ ID NO: 19 is the amino acid sequence of the reverse primer for pGST-azu 36-89.

SEQ ID NO: 20 is the amino acid sequence of the forward primer for pGST-azu 50-77.

SEQ ID NO: 21 is the amino acid sequence of the forward primer for pGST-azu 67-77.

SEQ ID NO: 22 is the amino acid sequence of the reverse primer for pGST-azu 50-77 and pGST-azu 67-77.

SEQ ID NO: 23 is the amino acid sequence of the forward primer for pGST-azu 50-66.

SEQ ID NO: 24 is the amino acid sequence of the reverse primer for pGST-azu 50-66.

SEQ ID NO: 25 is the amino acid sequence of the forward primer for the green fluorescent protein gene.

SEQ ID NO: 26 is the amino acid sequence of the reverse primer for green fluorescent protein gene.

SEQ ID NO: 27 is the amino acid sequence of the forward primer for gst-gfp-azu 50-77.

SEQ ID NO: 28 is the amino acid sequence of the reverse primer for gst-gfp-azu 50-77.

SEQ ID NO: 29 is the amino acid sequence of azurin from *Pseudomonas syringae*.

SEQ ID NO: 30 is the amino acid sequence of azurin/H.8 outer membrane protein from *Neisseria meningitides*.

SEQ ID NO: 31 is the amino acid sequence of the azurin from *Vibrio parahaemolyticus*.

SEQ ID NO: 32 is the amino acid sequence of the azurin from *Bordetella bronchiseptica*.

SEQ ID NO: 33 is the amino acid sequence of the auracyanin A from *Chloroflexus aurantiacus*

SEQ ID NO: 34 is the amino acid sequence of the auracyanin B from *Chloroflexus aurantiacus*.

SEQ ID NO: 35 is an artificial amino acid sequence representing the conserved residues in the cupredoxin entry domain where D is aspartic acid, G is glycine, Y is tyrosine, K is lysine and X is any amino acid.

SEQ ID NO: 36 is the amino acid sequence of the *Neisseria gonorrhoeae* Laz protein.

SEQ ID NO: 37 is the amino acid sequence of the 50-67 amino acid fragment of wt-azurin from *Pseudomonas aeruginosa*.

SEQ ID NO: 38 is the amino acid sequence of the 57-89 amino acid fragment of auracyanin B of *Chloroflexus aurantiacus*.

SEQ ID NO: 39 is the amino acid sequence of the 50-77 amino acid fragment of azurin from *Bordetella pertussis*.

SEQ ID NO: 40 is the amino acid sequence of the 106-132 amino acid fragment of the Laz protein from *Neisseria meningitidis*.

SEQ ID NO: 41 is the amino acid sequence of the 53-70 amino acid fragment of azurin from *P. aeruginosa*.

SEQ ID NO: 42 is the amino acid sequence of the 53-64 amino acid fragment of azurin from *P. aeruginosa*.

SEQ ID NO: 43 is the amino acid sequence of the azurin from *Bordetella pertussis*.

SEQ ID NO: 44 is the amino acid sequence of the 51-77 amino acid fragment from azurin from *P. aeruginosa*.

SEQ ID NO: 45 is the amino acid sequence of the 51-77 amino acid fragment from azurin from *Pseudomonas syringae*.

SEQ ID NO: 46 is the amino acid sequence of the is the 52-78 amino acid fragment from azurin from *Vibrio parahaemolyticus*.

SEQ ID NO: 47 is the amino acid sequence of the 51-77 amino acid fragment from azurin from *Bordetella bronchiseptica*.

SEQ ID NO: 48 is an artificial amino acid sequence representing the conserved residues in the cupredoxin entry domain where D is aspartic acid, G is glycine, Y is tyrosine, K is lysine and X is any amino acid.

BRIEF DESCRIPTION OF THE FIGURES

FIGS. 3(a), (b) and (c). (a) Diagram showing construction of a GST-GFP-azu 50-77 fusion protein. The gfp gene was introduced at the 3'-end of the gst gene (for GST-GFP) and the azu 50-77 fragment was then ligated at the 3'-end of the gfp gene in frame to produce the GST-GFP-azu 50-77 fusion protein. GST-GFP-azu 50-77 was purified as a single fusion protein from the cell lysates. Purified proteins were run on SDS-PAGE and detected by Coomassie Blue staining (9(b)) and also by Western blotting using anti-azurin antibody (9(c)).

FIG. 9 depicts a diagram of the Laz protein from *Neisseria meningitidis* and the azurin protein from *Pseudomonas aeruginosa*. The wording to the left of the bar indicates the name of the protein. The wording above the bars indicate the name of the region of the protein directly below in the bar. The numbers below the bar indicate the amino acid number of the junction of the regions of the protein.

FIG. 10 depicts the constructs of several azurin fusion proteins. The wording to left of the bar indicates the name of the construct, with plasmid and protein product indicated. The wording above the bar indicates the region of the protein depicted directly below in the bar. "N.Sp" indicates the *Neisseria gonorrhoeae* signal peptide; "H.8" indicates the H.8 region of *Neisseria gonorrhoeae*; "N.Azu" indicates *Neisseria gonorrhoeae* azurin; "P.Sp" indicates the *Pseudomonas aeruginosa* signal peptide; and "P. Azu" indicates the *P. aeruginosa* signal peptide.

DETAILED DESCRIPTION OF THE EMBODIMENTS

Figure 1A:
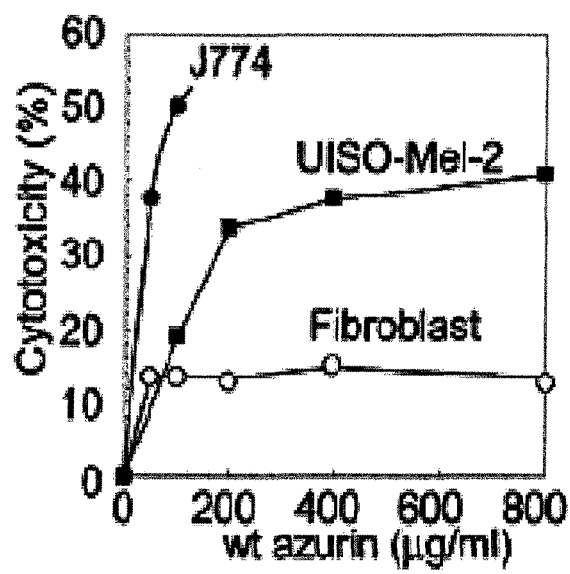
FIGS. 1(a) and (b). Graphs showing that entry of azurin correlates with cytotoxicity. (a) MTT assays were performed for the determination of wt-azurin-induced cytotoxicity against J774, UISOMel-2 and fibroblast cells. (b) Analysis of cell cycle progression in human normal fibroblast cells treated with M44KM64E mutant azurin. Fibroblast cells were incubated with 0 (control), 0.5 or 1.0 mg/ml of mutant azurin for 24 hr. At the end of the treatment, DNA content in the cells was determined by flow cytometry.

The present invention relates to methods and materials for delivering a cargo compound into a cell. Delivery of the cargo compound according to this invention is accomplished by the use of a suitable transport polypeptide. In one embodiment of the invention, the cargo compound is linked to the transport polypeptide. Suitable transport peptides include a cupredoxin, or a fragment of a cupredoxin containing a "cupredoxin entry domain". The term "cupredoxin entry domain" refers to a fragment of a cupredoxin that includes the amino sequence that is required for the entry of cupredoxin into a mammalian cancer cell. Cargo compounds delivered by the present invention include, but are not limited to, proteins, lipoproteins, polypeptides, peptides, polysaccharides, nucleic acids, including anti-sense nucleic acids, dyes, fluorescent and radioactive tags, microparticles or nanoparticles, toxins, inorganic and organic molecules, small molecules, and drugs. In some embodiments, the drugs and toxins kill tumor cells.

In one embodiment of the invention, the cupredoxin is an azurin, such as wt-azurin from *Pseudomonas aeruginosa*. "Wt-azurin" refers to wild-type azurin from *P. aeruginosa*. Similarly, the term "wt-azurin entry domain" refers to a fragment of wt-azurin that includes the amino sequence that is required for the entry of wt-azurin into a cell. In other embodiments of the invention, the cupredoxin is a plastocyanin, a rusticyanin, or a pseudoazurin, among others. In specific embodiments, the azurin is from *Pseudomonas aeruginosa, Pseudomonas syringa, Neisseria meningitides, Neisseria gonorrhoeae, Vibrio parahaemolyticus* or *Bordetella bronchiseptica*, among others.

In one embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell, among others. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A, among others. In other embodiments, a biologically active fragment of one of the above classes of compounds is delivered. In another embodiment, the cargo compound is delivered in order to generate an image of the target tissue. For example, the target tissue can be a cancer and the cargo compound can be one commonly used to generate an image for detection by X-ray computed tomography (CT), Magnetic Resonance Imaging (MRI) and ultrasound. In these embodiments, the cargo compound is a gamma ray or positron emitting radioisotope, a magnetic resonance imaging contrast agent, an X-ray contrast agent, or an ultrasound contrast agent.

Cupredoxins

"Cupredoxins" are small blue copper containing proteins having electron transfer properties (10-20 kDa) that participate in, for example, bacterial redox chains or photosynthesis. The copper ion is solely bound by the protein matrix. A special distorted trigonal planar arrangement to two histidine and one cysteinate ligands around the copper gives rise to very peculiar electronic properties of the metal site and an intense blue color. A number of cupredoxins have been crystallographically characterized at medium to high resolution. The cupredoxins include the azurins, plastocyanins, rusticyanins, pseudoazurins, auracyanins and azurin-like proteins. As used herein, the term "cupredoxin" includes the protein form without the copper atom present, as well as the copper containing protein.

Azurins

The azurins are copper containing proteins of 128 amino acid residues which belong to the family of cupredoxins involved in electron transfer in plants and certain bacteria. The azurins include those from *P. aeruginosa* (SEQ ID NO: 1)("wt-azurin"), *A. xylosoxidans*, and *A. denitrificans*. Murphy, L. M. et al., J. Mol. Biol. 315:859-71 (2002). Although the sequence homology between the azurins varies between 60-90%, the structural homology between these molecules is high. All azurins have a characteristic β-sandwich with Greek key motif and the single copper atom is always placed at the same region of the protein. In addition, azurins possess an essentially neutral hydrophobic patch surrounding the copper site (Murphy et al.).

Plastocyanins

The plastocyanins are cupredoxins that are found in eukaryotic plants and cyanobacteria. They contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 2 shows the amino acid sequence of plastocyanin from the cyanobacterium *Phormidium laminosum*.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths in plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. Redinbo et al., J. Bioenerg. Biomembr. 26(1):49-66 (1994).

Rusticyanins

Rusticyanins are blue-copper containing single-chain polypeptides obtained from a thiobacillus. The X-ray crystal structure of the oxidized form of the extremely stable and highly oxidizing cupredoxin rusticyanin from *Thiobacillus ferrooxidans* (SEQ ID NO: 3) has been determined by multiwavelength anomalous diffraction and refined to 1.9 Å resolution. The rusticyanins are composed of a core beta-sandwich fold composed of a six- and a seven-stranded β-sheet. Like other cupredoxins, the copper ion is coordinated by a cluster of four conserved residues (His85, Cys138, His143, Met148) arranged in a distorted tetrahedron. Walter, R. L. et al., J. Mol. Biol. 263:730-51 (1996).

Auracyanins

Three small blue copper proteins designated auracyanin A, auracyanin B 1, and auracyanin B-2 have been isolated from the thermophilic green gliding photosynthetic bacterium *Chloroflexus aurantiacus*. The two B forms have almost identical properties to each other, but are distinct from the A form. The sodium dodecyl sulfate-polyacrylamide gel electrophoresis demonstrates apparent monomer molecular masses as 14(A), 18 (B-2), and 22 (B-1) kDa.

The amino acid sequence of auracyanin A has been determined and showed auracyanin A to be a polypeptide of 139 residues. (Van Dreissche et al, Protein Science 8:947-957 (1999). His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 33 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. (Bond et al., J. Mol. Biol. 306:47-67 (2001).) With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. (J Biol Chem. 267:6531-6540 (1992).). See exemplary amino acid sequence SEQ ID NO: 34 for chain A of auracyanin B from *Chloroflexus aurantiacus* (NCBI Protein Data Bank Accession No. 1QHQA).

Pseudoazurins

The pseudoazurins are a family of blue-copper containing single-chain polypeptides. The amino acid sequence of pseudoazurin obtained from *Achromobacter cycloclastes* is shown in SEQ ID NO: 4. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Cytotoxic Activity of Cupredoxins

Cupredoxins have been studied extensively for their electron transfer (redox) properties but until recently were not known to exhibit cytotoxic effects. The present invention is predicated by the inventors' surprising discovery that cupredoxins as well as the iron (haem) containing redox protein cytochrome c551 induce either apoptosis or inhibit cell cycle progression in J774 mouse macrophage tumor cells and in human cancer cells. The redox activity of cupredoxins is not critical for their cytotoxic activity. For example, cupredoxins without a copper atom often exhibit a much lower redox activity compared to those containing the copper atom, but nevertheless demonstrate significant cytotoxic activity. In comparison to their activity in cancer cells, cupredoxins induce only a low level of apoptosis in vivo in normal tissues of tumor-bearing cupredoxin-treated mice.

The cytotoxic activity of cupredoxins is described in co-pending U.S. patent application Ser. No. 10/047,710, filed Jan. 15, 2002, and in co-pending U.S. patent application Ser. No. 10/720,603, filed Nov. 24, 2003. These prior applications are hereby incorporated by reference.

The present inventors now show that the selective effect of cupredoxins on cancer cells is related to the ability of cupredoxins to enter these cells. In Example 5, the inventors show that cupredoxins enter J774 cells. These cells are ascites forms of murine reticulum cell sarcoma with macrophage-like properties. In Examples 18 and 19, the inventors have shown that an azurin-like protein, the H.8 outer membrane from Neisseria, also know as Laz, can specifically enter brain tumor cells. In comparison, cupredoxins show an extremely reduced rate of entry into normal cells.

In one embodiment, the present invention relates to a "complex" containing a cupredoxin, or a fragment of a cupredoxin, linked to a "cargo compound" that is to be delivered into a cell. The cargo compound may be linked either covalently or non-covalently to form the complex. Methods of preparing such a complex are well known to those skilled in the art. For example, if the cargo compound is a protein or polypeptide, the complex can be formed as a fusion protein. Alternatively, the cargo compound may be covalently linked to the cupredoxin, or cupredoxin fragment, either directly or through a linker molecule, via, for example a disulfide or ester linkage.

Cupredoxin Entry Domain

The invention provides for a protein transduction domain that allows for the transport of linked cargo into mammalian cancer cells but not non-cancerous cells. It has been discovered that cupredoxin proteins comprise a protein transduction domain, the cupredoxin entry domain, which facilitates the entry of linked cargo into mammalian cancer cells. In some embodiments, the entire cupredoxin protein can be used to facilitate the transport linked cargo selectively into cancer cells. In other embodiments, a portion of a cupredoxin can be used to transport linked cargo into cancer cells. In some embodiments, the cupredoxin entry domain consists of a region of a cupredoxin that is less that the full length wild-type protein. In some embodiments, the cupredoxin entry domain consists more than about 10 residues, about 15 residues or about 20 residues of a cupredoxin. In some embodiments, the cupredoxin entry domain consists of not more than about 50 residues, about 40 residues or about 30 residues of a cupredoxin. In some embodiments, the cupredoxin entry domain has at least about 90% amino acid sequence identity, at least about 95% amino acid sequence identity or at least about 99% amino acid sequence identity to a cupredoxin.

As used herein, the terms "polypeptide," "peptide," and "protein" are used interchangeably to refer to a polymer of amino acid residues. A "polypeptide", "peptide" or "protein" may be synthesized within a cell and isolated from other proteins and cellular components. Alternatively, a "polypeptide", "peptide" or "protein" may be artificially synthesized according to methods well known to those in the art, and thus also be free of other proteins. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

The Examples describe a method of identifying fragments of *P. aeruginosa* wt-azurin that are suitable for use in the present invention. Such a method can also be used to identify fragments of other cupredoxins. Examples 1 and 2 describe the construction of a series of glutathione S-transferase ("GST") fusions of wt-azurin truncated at both the N- and the C-terminal. These examples also describe the purification of the fusion protein products.

Example 9 shows the internalization of such fusions in J774 cells at 37° C. While wt-azurin was internalized, GST remained at the periphery of the cells and was not internalized. azu 36-128 (SEQ ID NO: 5) and azu 36-89 (SEQ ID NO: 6) were internalized, as was azu 36-77 (SEQ ID NO: 7). Further truncations show that, while azu 50-77 (SEQ ID NO: 9) is internalized, the internalization of azu 36-50 (SEQ ID NO: 8) is highly inefficient. Further truncations of azu 50-77 (SEQ ID NO: 9) to azu 50-66 (SEQ ID NO: 10) and azu 67-77 (SEQ ID NO: 11) demonstrate very little internalization, indicating that efficient internalization requires not interfering with the sequence at or about positions 66-67. From a practical standpoint, the data support the use of amino acids 50 to 77 for efficient transport.

In some embodiments, the cupredoxin entry domain is a wt-azurin entry domain. In one embodiment of the present invention, a wt-azurin entry domain contains at least amino acids 50 to 77 of wt-azurin (SEQ ID NO: 9). In another embodiment of the invention, the wt-azurin entry domain contains at least amino acids 36 to 77 of wt-azurin (SEQ ID NO: 7). In another embodiment of the invention, the wt-azurin entry domain contains at least amino acids 36 to 89 of wt-azurin (SEQ ID NO: 6). In another embodiment of the invention, the wt-azurin entry domain contains at least amino acids 36 to 128 of wt-azurin (SEQ ID NO: 5). In yet another embodiment of the invention, the wt-azurin entry domain contains at least amino acids 50 to 67 of wt-azurin (SEQ ID NO: 37). In another embodiment of the invention, the wt-azurin entry domain contains at least amino acids 53 to 70 of wt-azurin (SEQ ID NO: 41). In yet another embodiment of the invention, the wt-azurin entry domain contains at least amino acids 53 to 64 of wt-azurin (SEQ ID NO: 42).

In another embodiment of the invention, the cupredoxin entry domain is an entry domain from a cupredoxin other than *P. aeruginosa* azurin. In different embodiments, the cupredoxin entry domain may be a fragment of plastocyanin from the cyanobacterium *Phormidium laminosum* (SEQ ID NO: 2), rusticyanin from *Thiobacillus ferrooxidans* (SEQ ID NO: 3); pseudoazurin from *Achromobacter cycloclastes* (SEQ ID NO: 4), azurin from *Pseudomonas syringae* (SEQ ID NO: 29), azurin from *Neisseria meningitidis* (SEQ ID NO: 30), azurin from *Neisseria gonnorhoeae* (SEQ ID NO: 36), azurin from *Vibrio parahaemolyticus* (SEQ ID NO: 31), azurin from *Bordetella bronchiseptica* (SEQ ID NO: 32), azurin from *Bordetella pertussis* (SEQ ID NO: 43) or an auracyanin from *Chloroflexus aurantiacus* (SEQ ID NO: 33 and 34).

In another embodiment of the invention, the cupredoxin entry domain contains at least amino acids 57 to 89 of auracyanin B of *Chloroflexus aurantiacus* (SEQ ID NO: 38). In another embodiment of the invention, the cupredoxin entry domain contains at least amino acids 50 to 77 of *Bordetella pertussis* (SEQ ID NO: 39). In another embodiment of the invention, the cupredoxin entry domain contains at least amino acids 106 to 132 of *N. meningitidis* (SEQ ID NO: 40). In another embodiment of the invention, the cupredoxin entry domain contains at least amino acids 51-77 of *Pseudomonas syringae* azurin (SEQ ID NO: 45). In another embodiment of the invention, the cupredoxin entry domain contains at least amino acids 89-115 of *Neisseria meningitidis* Laz (SEQ ID NO: 40). In another embodiment of the invention, the cupredoxin entry domain contains at least amino acids 52-78 of *Vibrio parahaemolyticus* azurin (SEQ ID NO: 46). In another embodiment of the invention, the cupredoxin entry domain contains at least amino acids 51-77 of *Bordetella bronchiseptica* azurin (SEQ ID NO: 47).

Modification of a Cupredoxin Entry Domain

In another embodiment of the present invention, a cupredoxin entry domain is chemically modified or genetically altered to produce variants that retain the ability to transport a cargo compound into a cell. For example, Example 14 shows that wt-azurin having proline residues introduced at positions 54, 61 and 70 retains its ability to enter UISO-Mel-2 cells.

In another embodiment, the cupredoxin entry domain comprises a conserved amino acid sequence DGXXXXXDXX-YXKXXD (SEQ ID NO: 35) or DGXXXXDXXYXKXXD (SEQ ID NO: 48) where D is aspartic acid, G is glycine, Y is tyrosine, K is lysine and X is any amino acid. See Example 17.

Variants of a cupredoxin entry domain may be synthesized by standard techniques. Derivatives are amino acid sequences formed from native compounds either directly or by modification or partial substitution. Analogs are amino acid sequences that have a structure similar, but not identical, to the native compound but differ from it in respect to certain components or side chains. Analogs may be synthesized or from a different evolutionary origin.

Variants may be full length or other than full length, if the derivative or analog contains a modified amino acid. Variants of a cupredoxin entry domain include, but are not limited to, molecules comprising regions that are substantially homologous to the cupredoxin entry domain by at least about 65%, 70%, 75%, 85%, 90%, 95%, 98%, or 99% identity over an amino acid sequence of identical size or when compared to an aligned sequence in which the alignment is performed by a homology algorithm.

The term "percent (%) amino acid sequence identity" between a cupredoxin entry domain and a candidate sequence is defined as the percentage of amino acid residues in a cupredoxin entry domain that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\% \text{ amino acid sequence identity} = X/Y \cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Changes can be introduced into a cupredoxin entry domain that incur alterations in the amino acid sequences of the cupredoxin entry domain that do nullify the ability of the cupredoxin entry domain to transport a cargo compound into a cell. A "non-essential" amino acid residue is a residue that can be altered from the sequence of the cupredoxin entry domain without nullifying its ability to transport a cargo compound into a cell, whereas an "essential" amino acid residue is required for such activity.

Amino acids for which "conservative" substitutions can be made are well known in the art. Useful conservative substitutions are shown in Table 1, "Preferred substitutions." Conservative substitutions whereby an amino acid of one class is replaced with another amino acid of the same class fall within the scope of the invention so long as the substitution does not nullify the activity of the cupredoxin entry domain. Such exchanges that result in altered cupredoxin entry domain activity are contemplated as part of the invention so long as such activity is appreciable.

TABLE 1

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

"Non-conservative" substitutions that affect (1) the structure of the polypeptide backbone, such as a n-sheet or a-helical conformation, (2) the charge, (3) hydrophobicity, or (4) the bulk of the side chain of the target site can modify the cupredoxin entry domain function. Residues are divided into groups based on common side-chain properties as denoted in Table 2. Non-conservative substitutions entail exchanging a member of one of these classes for another class.

Non-conservative substitutions whereby an amino acid of one class is replaced with another amino acid of a different class fall within the scope of the invention so long as the substitution does not nullify the activity of the cupredoxin entry domain. Such exchanges that result in altered cupredoxin domain activity are contemplated as part of the invention so long as such activity is appreciable.

TABLE 2

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

In another embodiment, the variants of a cupredoxin entry domain have a significant structural similarity to *P. aeruginosa* azurin residues 50-77. Examples of studies that determine significant structural homology between cupredoxins and other proteins include Toth et al. (Developmental Cell 1:82-92 (2001)). Specifically, significant structural homology between a variant of the cupredoxin entry domain and *P. aeruginosa* azurin residues 50-77 is determined by using the VAST algorithm (Gibrat et al., Curr Opin Struct Biol 6:377-385 (1996); Madej et al., Proteins 23:356-3690 (1995)). In specific embodiments, the VAST p value from a structural comparison of a variant of the cupredoxin entry domain and *P. aeruginosa* azurin residues 50-77 is less than about $10^{-3}$, less than about $10^{-5}$, or less than about $10^{-7}$. In other embodiments, significant structural homology between a variant of the cupredoxin entry domain and *P. aeruginosa* azurin residues 50-77 can be determined by using the DALI algorithm (Holm & Sander, *J. Mol. Biol.* 233:123-138 (1993)). In specific embodiments, the DALI Z score for a pairwise structural comparison is at least about 3.5, at least about 7.0, or at least about 10.0.

Modifications to the cupredoxin entry domain can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-50 (1987)), cassette mutagenesis, restriction selection mutagenesis (Wells et al., Gene 34:315-23 (1985)) or other known techniques can be performed on the cloned DNA to produce a cupredoxin entry domain variant nucleic acid. In addition, nucleotides encoding entry domains with structural similarity to that of the cupredoxin entry domains may be synthesized by methods that are well known in the art. Further, protein molecules that are wild type or variant cupredoxin entry domains may be synthesized by methods that are well known in the art.

Nucleic Acids Coding for a the Cupredoxin Entry Domain and Complex of a Cupredoxin Entry Domain Linked to a Cargo Compound In another aspect, the present invention provides a nucleic acid molecule encoding a fusion protein comprising a cupredoxin entry domain linked to a cargo compound, where the cargo compound is a protein or peptide. The nucleic acid molecule according to the invention can be prepared by a combination of known techniques in the art. For instance, nucleic acid sequences for the cupredoxin entry domain and the cargo compound can individually be prepared by chemical synthesis or cloning. The nucleic acid sequences are then ligated in order with a ligase to give a nucleic acid molecule of interest.

Methods of Delivering a Cargo Compound using a Cupredoxin Entry Domain

Many arginine-rich peptides are known to translocate through mammalian cell membranes and carry protein cargo compounds inside such cells. Suzuki, T., et al. J. Biol. Chem. 277:2437-43 (2002). For example, a short arginine-rich 11 amino acid (amino acids 47-57) segment of HIV Tat protein allows transport of cargo proteins into mammalian cells. Schwarze, S R., et al. Trends Cell Biol. 10:290-95 (2000). Synthetic entry domains that strengthen the alpha-helical content and optimize the placement of arginine residues have been shown to have enhanced potential as protein transduction domains. Ho, A., et al. Cancer Res. 61:474-77 (2001). In comparison, wt-azurin has a single arginine residue. It is therefore believed, but not relied upon for the present invention, that its mode of entry is different from that of the Tat protein.

The present invention encompasses the use of those cupredoxin fragments that facilitate the entry of a cargo compound into a cell. Such fragments may be determined by any method that identifies those fragments required for entry into a cell. In one such method, a cupredoxin fragment is linked to a marker substance and a test performed to determine whether the cupredoxin fragment enters a cell. Such methods may be used to identify suitable fragments of the cupredoxins discussed above.

In various embodiments of the present invention, the cargo compound is attached to a cupredoxin, such as azurin from *P. aeruginosa* (SEQ ID NO: 1)("wt-azurin"); plastocyanin from the cyanobacterium *Phormidium laminosum* (SEQ ID NO: 2); rusticyanin from *Thiobacillus ferrooxidans* (SEQ ID NO: 3); or pseudoazurin from *Achromobacter cycloclastes* (SEQ ID NO: 4), azurins from *Pseudomonas syringa* (SEQ ID NO: 29), *Neisseria meningitidis* (SEQ ID NO: 30), *Vibrio parahaemolyticus* (SEQ ID NO: 31), *Bordetella bronchiseptica* (SEQ ID NO: 32), auracyanin A and B from *Chloroflexus aurantiacus* (SEQ ID NO. 33 and 34) or *Neisseria gonorrhoeae* (SEQ ID NO. 36), among other azurin and azurin-like proteins. In other embodiments, the cargo is linked to a cupredoxin entry domain.

In various embodiments of the present invention, a cupredoxin entry domain delivers a cargo compound into a cell in vitro, ex vivo or in vivo. For example, delivery may be achieved in vitro by adding a complex of a cupredoxin entry domain and a cargo compound to a cell culture, such as a pap smear. Alternatively, delivery may be achieved ex vivo by adding the complex to a sample removed from a patient, for example, blood, tissue, or bone marrow, and returning the treated sample to the patient. Delivery may also be achieved by administration of the complex directly to a patient. The methods of the present invention may be used for therapeutic, prophylactic, diagnostic or research purposes. Cargo compounds delivered by the present invention include, but are not limited to, proteins, lipoproteins, polypeptides, peptides, polysaccharides, nucleic acids, including anti-sense nucleic acids, dyes, microparticles or nanoparticles, toxins, organic and inorganic molecules, small molecules, and drugs.

In one embodiment, a detectable substance, for example, a fluorescent substance, such as green fluorescent protein; a luminescent substance; an enzyme, such as β-galactosidase; or a radiolabelled or biotinylated protein is delivered to confer a detectable phenotype to a cell. Similarly, microparticles or nanoparticles labeled with a detectable substance, for example, a fluorescent substance, can be delivered. One example of suitable nanoparticles is found in U.S. Pat. No. 6,383,500, issued May 7, 2002, which is hereby expressly incorporated by reference. Many such detectable substances are known to those skilled in the art.

In some embodiments, the cargo compound is a detectable substance that is suitable for X-ray computed tomography, magnetic resonance imaging, ultrasound imaging or radionuclide scintigraphy. In these embodiments, the cargo compound is administered to the patient for purposes of diagnosis. A contrast agent is administered as a cargo compound to enhance the image obtained by X-ray CT, MRI and ultrasound. The administration of a radionuclide cargo compound that is targeted to tumor tissue via the cupredoxin entry domain can be used for radionuclide scinitigraphy. In some embodiments, the cupredoxin entry domain may contain the radionucleotide with or without a cargo compound. In other embodiments, the cargo compound is a gamma ray or positron emitting radioisotope, a magnetic resonance imaging contract agent, an X-ray contrast agent, or an ultrasound contrast agent.

Ultrasound contrast agents suitable for use as cargo compounds include, but are not limited to, a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein expressly incorporated by reference. The term surfactant microsphere includes nanospheres, liposomes, vesicles and the like. The biocompatible gas can be air, or a fluorocarbon, such as a $C_3$-$C_5$ perfluoroalkane, which provides the difference in echogenicity and thus the contrast in ultrasound imaging. The gas is encapsulated or contained in the microsphere to which is attached the cupredoxin entry domain, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents suitable for use as cargo compounds include, but are not limited to, one or more X-ray absorbing or "heavy" atoms of atomic number 20 or greater, further comprising an optional linking moiety, $L_n$, between the cupredoxin entry domain and the X-ray absorbing atoms. The frequently used heavy atom in X-ray contrast agents is iodine. Recently, X-ray contrast agents comprised of metal chelates (e.g., U.S. Pat. No. 5,417,959) and polychelates comprised of a plurality of metal ions (e.g., U.S. Pat. No. 5,679,810) have been disclosed. More recently, multinuclear cluster complexes have been disclosed as X-ray contrast agents (e.g., U.S. Pat. No. 5,804,161, PCT WO91/14460, and PCT WO 92/17215).

MRI contrast agents suitable for use as cargo compounds include, but are not limited to, one or more paramagnetic metal ions, further comprising an optional linking moiety, $L_n$, between the cupredoxin entry domain and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

In another embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A. In other embodiments, a biologically active fragment of one of the above classes of compounds is delivered.

In yet another embodiment, the cargo compound is a nucleic acid coding for one of the above classes of compounds. In yet another embodiment, the cargo compound is a drug used to treat cancer. Such drugs include, for example, 5-fluorouracil; Interferon α; Methotrexate; Tamoxifen; and Vincristine. The above examples are provided for illustration only, many other such compounds are known to those skilled in the art.

Cargo compounds suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17.beta.-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful as cargo compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The above other therapeutic agents, when employed as cargo compounds with the compounds of the present invention, may be used, for example, in those amounts indicated in the Physicians' Desk Reference (PDR) or as otherwise determined by one of ordinary skill in the art.

Pharmaceutical Compositions Containing a Cupredoxin Entry Domain

Pharmaceutical compositions containing a complex of a cupredoxin entry domain linked to a cargo compound can be manufactured in any conventional manner, e.g., by conventional mixing, dissolving, granulating, dragee-making, emulsifying, encapsulating, entrapping, or lyophilizing processes. The complex can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also include, for example, fillers and cellulose preparations. Other excipients can include, for example, flavoring agents, coloring agents, detackifiers, thickeners, and other acceptable additives, adjuvants, or binders.

Such compositions can be used in, for example, the detection or imaging of a cell type or in the treatment of a condition related to cell death or in the prevention thereof. The compositions can be administered in an amount sufficient to prevent or treat a condition related to resistance to cell death. As used herein, the term "a condition related to resistance to cell death" refers to a disease, state, or ailment characterized by at least a tendency for prolonged cell life when compared with a healthy cell of like kind as determined by a reasonable, skilled physician or clinician. Typically, the host organism is a mammal, such as a human or animal.

Administration of Compositions Containing a Cupredoxin Entry Domain

Compositions containing a cupredoxin entry domain can be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary administration). The compositions and pharmaceutical formulations thereof can be administered in any amount effective to achieve its intended purpose. When administrated to treat a condition related to resistance to cell death, the composition is administered in a therapeutically effective amount. A "therapeutically effective amount" is an amount effective to prevent development of, or to alleviate the existing symptoms of, the subject being treated. Determination of a therapeutically effective amount is well within the capability of those skilled in the art.

In various embodiments, the composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the compositions of this invention. Suitable biodegradable microspheres are shown, for example, in U.S. Pat. Nos. 4,897,268, 5,075,109, 5,928,647, 5,811,128, 5,820,883, 5,853,763, 5,814,344 and 5,942,252. "Compounds" as used herein, include the peptides, amino acid sequences, cargo compounds and complexes of the present invention The half-life in the bloodstream of the compositions of the invention can be extended or optimized by several methods well known to those in the art, including but not limited to, circularized peptides (Monk et al., BioDrugs 19(4):261-78, (2005); DeFreest et al., J. Pept. Res. 63(5):409-19 (2004)), D,L-peptides (diastereomer), (Futaki et al., J. Biol. Chem. February 23; 276(8):5836-40 (2001); Papo et al., Cancer Res. 64(16):5779-86 (2004); Miller et al, Biochem. Pharmacol. 36(1):169-76, (1987)); peptides containing unusual amino acids (Lee et al., J. Pept. Res. 63(2):69-84 (2004)), and N- and C-terminal modifications (Labrie et al., Clin. Invest. Med. 13(5):275-8, (1990)). Of particular interest are d-isomerization (substitution) and modification of peptide stability via D-substitution or L-amino acid substitution.

The compositions of the invention may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions of the invention may be administered in a variety of ways, including by injection (e.g., intradermal, subcutaneous, intramuscular, intraperitoneal and the like), by inhalation, by topical administration, by suppository, by using a transdermal patch or by mouth.

When administration is by injection, composition may be formulated in aqueous solutions, preferably in physiologically compatible buffers such as Hanks solution, Ringer's solution, or physiological saline buffer. The solution may contain formulatory agents such as suspending, stabilizing and/or dispersing agents. Alternatively, the composition may be in powder form for constitution with a suitable vehicle, e.g., sterile pyrogen-free water, before use.

When administration is by inhalation, the composition may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

When administration is by topical administration, the composition may be formulated as solutions, gels, ointments, creams, suspensions, and the like, as are well known in the art. In some embodiments, administration is by means of a transdermal patch. When administration is by suppository (e.g., rectal or vaginal), composition may also be formulated in compositions containing conventional suppository bases.

When administration is oral, the composition can be readily formulated in combination with pharmaceutically acceptable carriers well known in the art. A solid carrier, such as mannitol, lactose, magnesium stearate, and the like may be employed; such carriers enable the chemotaxin to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include the composition allow for the release of the composition over extended periods of time, such that without the sustained release formulation, composition would be cleared from a subject's system, and/or degraded by, for example, proteases and simple hydrolysis before eliciting or enhancing an therapeutic effect.

The exact formulation, route of administration, and dosage is determined by the attending physician in view of the patient's condition. Dosage amount and interval can be adjusted individually to provide plasma levels of the complex which are sufficient to maintain therapeutic effect. Generally, the desired composition is administered in an admixture with a pharmaceutical carrier selected with regard to the intended route of administration and standard pharmaceutical practice.

The appropriate dosage will, of course, vary depending upon, for example, the compound containing the cupredoxin entry domain employed, the host, the mode of administration and the nature and severity of the conditions being treated or diagnosed. However, in one embodiment of the methods of the present invention, satisfactory treatment results in humans are indicated to be obtained at daily dosages from about 0.001 to about 20 mg/kg of body weight of the compound containing the cupredoxin entry domain. In one embodiment, an indicated daily dosage for treatment in humans may be in the range from about 0.7 mg to about 1400 mg of a compound containing the cupredoxin entry domain conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days. Dosing can be continuous, intermittent or a single dose, using any applicable dosing form, including tablet, patches, i.v. administration and the like. More specifically, the composition is administered in a therapeutically effective amount. In specific embodiments, the therapeutically effective amount is from about 0.01-20 mg/kg of body weight. In specific embodiments, the dose level is about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

The method of introducing compounds containing the cupredoxin entry domain to patients is, in some embodiments, co-administration with other drugs known to treat cancer. Such methods are well-known in the art. In a specific embodiment, the compounds containing the cupredoxin entry domain are part of an cocktail or co-dosing containing or with other drugs for treating cancer. Such drugs include, for example, those listed herein and specifically 5-fluorouracil; Interferon α; Methotrexate; Tamoxifen; and Vincristine. The above examples are provided for illustration only, many other such compounds are known to those skilled in the art.

Other drugs suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17.beta.-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy and surgery.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful to co-administer with the compositions of the invention include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical techniques, especially in the treatment of cancer).

Pharmaceutical compositions used in accordance with the present invention can be formulated in a conventional manner using one or more physiologically acceptable carriers comprising excipients and auxiliaries that facilitate processing of the composition, active agents, for inhibiting or stimulating the secretion of the composition, or a mixture thereof into preparations which can be used therapeutically.

Nucleic acid molecules encoding a cupredoxin entry domain or a fusion protein combining a either entry domain and a cargo compound can be inserted into vectors and used as gene therapy vectors. Gene therapy vectors can be delivered to a subject by, for example, intravenous injection, local administration (Nabel et al., U.S. Pat. No. 5,328,470 1994. USA), or by stereotactic injection (Chen et al., Proc Natl Acad Sci USA, vol. 91, pp 3054-57 (1994)). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one aspect, the composition is delivered as DNA such that the complex is generated in situ. In one embodiment, the DNA is "naked," as described, for example, in Ulmer et al., *Science* 259:1745-49 (1993) and reviewed by Cohen, *Science* 259 1691-92 (1993). The uptake of naked DNA may be increased by coating the DNA onto a carrier, e.g. a biodegradable bead, which is efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of the composition. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a composition polynucleotide to an inducible promoter can control the expression of the wt-azurin entry domain composition polypeptide or fragments. Examples of classic inducible promoters include those that are responsive to α-interferon, heat shock, heavy metal ions, and steroids such as glucocorticoids (Kaufman, *Methods Enzymol.* 185: 487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, enhancer elements, promoters, and transcription termination sequences.

Kits Comprising a Cupredoxin Entry Domain-Cargo Compound Complex

In another aspect, the invention provides kits containing one or more of the following in a package or container: (1) a reagent comprising a complex of a cupredoxin entry domain linked to a cargo compound; (2) a reagent containing a pharmaceutically acceptable adjuvant or excipient; (3) a vehicle for administration, such as a syringe; (4) instructions for administration. Embodiments in which two or more of components (1)-(4) are found in the same container are also contemplated.

When a kit is supplied, the different components of the composition may be packaged in separate containers and admixed immediately before use. Such packaging of the components separately may permit long-term storage without losing the active components' functions.

The reagents included in the kit can be supplied in containers of any sort such that the life of the different components are preserved and are not adsorbed or altered by the materials of the container. For example, sealed glass ampules may contain lyophilized polypeptide or polynucleotide, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended embodiments.

EXAMPLES

Example 1

Plasmid Constructions

Plasmids expressing fusion glutathione S-transferase (GST)-truncated wt-azurin (azu) derivatives were constructed by a polymerase chain reaction using proofreading DNA polymerase. FIG. 6 shows a schematic representation of various truncated wt-azurin constructs. For pGST-azu 36-128, an amplified PCR fragment was introduced into the BamHI and EcoRI sites of the commercial GST expression vector pGEXSX (Amersham Biosciences, Piscataway, N.J. 08855). The fragment was amplified with pUC19-azu as a template and primers, 5'-CGGGATCC CCG GCA ACC TGC CGA AGA ACG TCA TGG GC-3'(SEQ ID NO: 12) and 5'-CGGAATTC GCA TCA CTT CAG GGT CAG GG-3' (SEQ ID NO: 13), where the additionally introduced BamHI and EcoRI sites are underlined respectively. Carboxyl-terminus truncation of azu gene was cumulatively performed by introducing a stop codon using QuickChange site-direct mutagenesis kit (Stratagene, La Jolla, Calif. 92037).

For pGST-azu 36-50, pGST-azu 36-77 and pGST-azu 36-89, stop codons were introduced into Ser51, Ser78, and Gly90, respectively. The plasmid carrying pGST-azu 36-128 was used as template DNA. Three sets of oligonuclotides for site-direct mutagenesis are shown as follows. For pGST-azu 36-50: 5'-GGC CAC AAC TGG GTA CTG TGA ACC GCC GCC GAC ATG CAG-3' (SEQ ID NO: 14), and 5'-CTG CAT GTC GGC GGC GGT TCA CAG TAC CCA GTT GTG GCC-3' (SEQ ID NO: 15). For pGST-azu 36-77: 5'-CCT GAA GCC CGA CGA CTG ACG TGT CAT CGC CCA CAC C-3' (SEQ ID NO: 16) and 5'-GGT GTG GGC GAT GAC ACG TCA GTC GTC GGG CTT CAG G-3' (SEQ ID NO: 17). For pGST-azu 36-89: 5'-CCA AGC TGA TCG GCT CGT GAG AGAAGG ACT CGG TGA CC-3' (SEQ ID NO: 18), and 5'-GGT CAC CGA GTC CTT CTC TCA CGA GCC GAT CAG CTT GG-3 (SEQ ID NO: 19). The plasmids pGST-azu 50-77 and pGST-azu 67-77 were generated by PCR using pGST-azu 36-77 as a template DNA.

Amplified PCR fragments, azu 50-77 and am 67-77, were obtained using forward primers 5'-CGGGATCC TGA GCA CCG CCG CCG ACA TGC AGG G-3' (SEQ ID NO: 20) and 5'-CGGGATCC CCG GCC TGG ACA AGG ATT ACC TGA AGC CCG-3 (SEQ ID NO: 21), where the additionally introduced BamHI site is indicated by underlining. The reverse primer, 5'-CGGAATTC GCA TCA CTT CAG GGT CAG GG-3' (SEQ ID NO: 22), was utilized in both cases.

The plasmid carrying gst-azu 50-77 was used for generating pGST-azu 50-66 by introduction of a stop codon in Gly67 using oligonuclotides as follows: 5'-GAC GGC ATG GCT TCC TGA CTG GAC AAG GAT TAC C-3' (SEQ ID NO: 23), and 5'-GGT AAT CCT TGT CCA GTC AGG AAG CCA TGC CGTC-3' (SEQ ID NO: 24). The green fluorescent protein gene (gfp) encoding the green fluorescent protein was also amplified by PCR. Forward and reverse primers used were 5'-CGGGATCC CCA TGG TGA GCA AGGGCG-3' (SEQ ID NO: 25) and 5'-CGGAATTC CTT GTA CAG CTC GTC CAT GCC G-3' (SEQ ID NO: 26) containing BamHI and EcoRI sites at the 5' end of each oligonuclotides. The resultant PCR fragment was ligated into the pGEXSX vector for creating pGST-GFP. For the preparation of plasmid DNA carrying gst-gfp-azu 50-77, the azu 50-77 gene was amplified by PCR with pGST-azu 50-77 as a template and primers 5'-CCGCTCGAG CCT GAG CAC CGC CGC CATGCA GGG-3' (SEQ ID NO: 27) and 5'-TTTTCCTTTTGC GGCCGC TCA GTC GTC GGG CTT CAG GTA ATC C-3' (SEQ ID NO: 28), where the introduced Xho I and Not I sites are underlined respectively. Purified azu 50-77 fragment was introduced into pGST-GFP at Xho I and Not I unique restriction enzyme sites Example 2

Purification of Proteins

Wt-azurin and M44KM64E mutant azurin were prepared and purified as described by Yamada, T. et al. Proc. Natl. Acad. Sci. USA, vol. 101, pp. 4770-75 (2004), and in copending U.S. patent application Ser. No. 10/720,603, the contents of which are incorporated by this reference. Briefly, the wt-azurin gene was amplified by PCR according to the method described by Kukimoto et al., FEBS Lett, vol. 394, pp 87-90 (1996). PCR was performed using genomic DNA from *P. aeruginosa* strain PAO1 as a template DNA.

The amplified DNA fragment of 545 bp, digested with HindIII and PstI, was inserted into the corresponding sites of pUC19 so that the azurin gene was placed downstream of the lac promoter to yield an expression plasmid pUC19-azuA. *E. col* JM109 was used as a host strain for expression of the azurin gene. The recombinant *E. coil* strain was cultivated in 2YT medium containing 50 μg ml$^{-1}$ ampicillin, 0.1 mM IPTG; and 0.5 mM $CuSO_4$ for 16 h at 37° C. to produce azurin.

For preparation of the M44KM64E mutant azurin, site-directed mutagenesis of the azurin gene was performed using a QuickChange site-directed mutagenesis kit (Stratagene, La Jolla, Calif.). Mutations were confirmed by DNA sequencing.

Plasmid DNA, pET9a carrying the rus gene encoding the cupredoxin rusticyanin from *Acidithiobacillus ferrooxidans*, was obtained from Dr. Kazuhiko Sasaki, Central Research Institute of Electric Power Industry, Chiba, Japan.

Rusticyanin was isolated from *E. coli* BL21 (DE3) harboring the rus gene using the method of Sasaki, K., et al. Biosci. Biotechnol. Biochem., vol. 67, pp. 1039-47 (2003) with some modifications. Briefly, acetic acid buffer (pH 4.0) and CM-Sepharose (Sigma Chemicals, St. Louis, Mo. 63178) were used instead of beta-alanin buffer (pH 4.0) and TSK-gel CM-650 column (Tosoh Bioscience, LLC, Montgomeryville, Pa. 18936). Two other purified cupredoxins, plastocyanin from *Phormidium laminosum* and pseudoazurin from *Achromobacter cycloclastes* were obtained from Dr. Beatrix G. Schlarb-Ridley, University of Cambridge, UK and Dr. Christopher Dennison, University of Newcastle Upon Tyne, UK, respectively.

All recombinant GST-fusion derivatives were purified as follows: *E. coli* BL21 cells were used as the host strain. After induction with 0.4 mM IPTG at early log phase of growth in L broth, GST-fusion proteins were purified from cell extracts by using Glutathione Sepharose 4B affinity chromatography and Sephadex 75 gel-filtration column with PBS (Amersham Biosciences, Piscataway, N.J. 08855). Purified proteins, wt azurin and GST-derivatives or other cupredoxins, labeled with ALEXA FLUOR® (Molecular Probes, Inc., Eugene, Oreg. 97402) were isolated according to manufacturer's instructions. Unbound free fluorescent chemical was removed by gel-filtration column.

Example 3

Cell Cultures

J774 and UISO-Mel-2 cells (available from Frederick Cancer Research and Development Center, Frederick, Md. U.S.A.) were cultured as described in Yamada, T. et al. Infect. Immun. vol. 70, pp. 7054-62 (2002); Goto, M., et al. Mol. Microbiol. vol. 47, pp. 549-59 (2003); and Yamada, T., et al. Proc. Natl. Acad. Sci. USA vol. 99, pp. 14098-103 (2002), the contents of which are incorporated by reference. Human normal fibroblast cells (stock culture collection of the Department of Surgical Oncology, University of Illinois at Chicago (UIC), Chicago) were cultured in MEM with Eagle's salt containing 2 mM L-glutamine, 0.1 mM MEM essential amino acids and supplemented with 10% heat inactivated fetal bovine serum, 100 Units/ml penicillin and 100 μg/ml streptomycin. MCF-7 and MOF-10F cells were cultured as described in Punj et al. *Oncogene* 23:2367-78 (2004).

Example 4

Co-Culture of J774, UISO-Mel-2 and Fibroblast Cells and Confocal Microscopy

J774, UISO-Mel-2, and fibroblast cells were cultured on individual cover slips. After overnight incubation, the cells were washed with fresh media and all three cell lines were placed on a culture dish containing 200 μg/ml of wt-azurin conjugated with ALEXA FLUOR® 568. The cells were then incubated for 0.5 or 3.5 h at 37° C. under 5% $CO_2$.

For preparation of microscope samples, cells were cultured on cover-slips overnight at 37° C. Cultured cells were placed at 37° C. or 4° C. for 2 h before protein treatment. Pre-warmed 37° C. fresh media or ice-cold 4° C. fresh media were mixed with red-fluorescent (labeled with ALEXA FLUOR® 568) cupredoxins or GST-fusion derivatives, and incubated with the cells. The cells were washed with PBS, and fixed with methanol at −20° C. for 5 min. After washing with PBS twice and the addition of mounting media containing 1.5 μg/ml 4',6-diamidino-2-phenylindole (DAPI) for staining nuclei (VECTASHILD, Vector, Burlingame, Calif.), images were taken by a confocal microscope.

Example 5

Entry of Cupredoxins into J774 Cells

Wt-azurin, its mutant variant M44KM64E, plastocyanin, pseudoazurin and rusticyanin were incubated with J774 cells as in Example 4 and the cells examined using confocal microscopy. In these experiments, the cupredoxins were conjugated with ALEXA FLUOR® 568 to fluoresce red and incubated with the J774 cells for 1 hr at 37° C. at a concentration of 200 μg/ml, and in a separate experiment wild type azurin and rusticyanin were incubated with J774 cells for 1 hr at 37° C. at a concentration of about 6 to 7 μM. The nucleus was stained blue with DAPI. A control without the proteins was maintained. In all cases, the cupredoxins were seen to enter into the cytosol of J774 cells. In similar experiments, auracyanin A and B enter preferentially to MCF7 cancer cells and not non-cancerous control cells.

Example 6

Entry of Wt-Azurin and Rusticyanin into Various Cell Types

Wt-azurin exhibits a reduced cytotoxic activity towards MCF-10F cells as contrasted with the MCF-7 cells. Punj et al. *Oncogene* 23:2367-2378 (2004). J774, peritoneal macrophages, mast cells, human breast cancer MCF-7 and human normal epithelial MCF-10F cells (stock culture collection of the Department of Surgical Oncology, University of Illinois at Chicago (UIC), Chicago) were treated and examined as in Example 5 and tested to determine if wt-azurin could enter such cells.

Wt-azurin was internalized in J774 cells during 45 mm incubation. However, it was internalized very inefficiently in peritoneal macrophages or mast cells. Even after 6 hr incubation, such cells showed only limited entry. Similarly, while wt-azurin entered the breast cancer MCF-7 cells efficiently, it showed an extremely reduced rate of entry in the normal mammary MCF-10F cells.

Alexa Fluor®-conjugated azurin entered efficiently in UISOMel-2 and MCF-7 cancer cells but not in the normal mammary MCF 10A1 cells. Alexa Fluor®-conjugated rusticyanin, however, not only entered the cytosol of UISO-Mel-2 and MCF-7 cancer cells, but also in the normal MCF 10A1 cells. Unlike in the cancer cells where rusticyanin was evenly distributed in the cytosol, in MCF10A1 cells, much of the rusticyanin was sequestered in the perinuclear space surrounding the nucleus.

Example 7

Wt Azurin-Mediated Cytotoxicity and Growth Inhibition

To further assess the specificity of entry of wt-azurin in various cells, we determined the entry of Alexa fluor-conjugated wt-azurin in J774, UISO-Mel-2 and normal fibroblast cells during incubation at 37° C. for 30 min and 3.5 hr. Wt-azurin was seen to enter rapidly in J774 and UISO-Mel-2 cells in 30 mm; very little wt-azurin was seen in the cytosol of fibroblasts during this period. After 3.5 hr of incubation, only small amounts of wt-azurin were found in the fibroblasts.

Figure 1B:
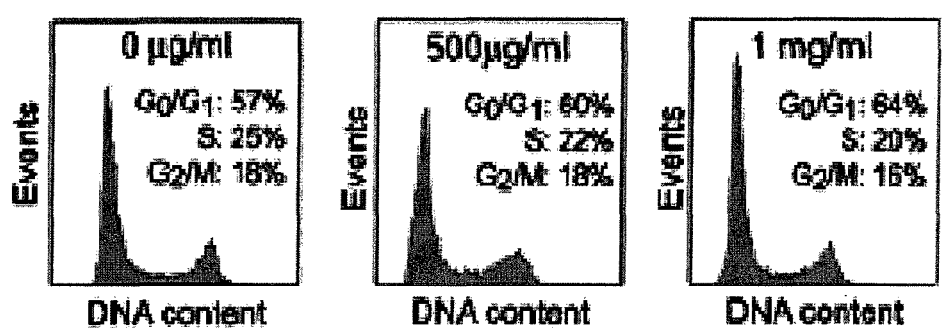

A 3(4,5 dimethylthiazol-2-y-2,5 tetrazolium bromide) (MTT) assay was performed for the measurement of the cytotoxicity of wt-azurin as described by Yamada, T., et al. *Infect. Immun.* 70:7054-62 (2002), Goto, M., et al. *Mol. Microbiol* 47:549-59 (2003), and in co-pending U.S. patent application Ser. No. 10/720,603, filed Nov. 24, 2003, the contents of which are incorporated by reference. FIG. 1(b) shows that significant wt-azurin-mediated cytotoxicity was observed only with J774 and UISO-Mel-2 cells during 24 hr incubation.

M44KM64E mutant azurin showed very little apoptosis-inducing activity in J774 cells but at 1 mg/ml concentration significantly inhibited (about 95%) cell cycle progression at the $G_1$ to S phase. Cell cycle progression was analyzed by flow cytometry, as described by Hiraoka, Y. et al., *Proc. Natl. Acad. Sci. USA*, vol. 101:6427-32 (2004) and Yamada, T. et al. *Proc. Natl. Acad. Sci. USA* 101:4770-75 (2004), the contents of which are incorporated by reference. FIG. 1(a) shows that when the fibroblasts were treated with 500 μg/ml or 1 mg/ml of M44KM64E mutant azurin, the extent of inhibition of cell cycle progression was about 20%.

Example 8

Microinjection of Wt-Azurin into Fibroblast and MCF-10F Cells

Wt-azurin was microinjected into fibroblast and MCF-10F cells as using the method described by Punj, V., et al., *Oncogene* 23:2367-78 (2004). Cells were examined for induction of apoptosis, leading to nuclear DNA condensation and fragmentation. Significant nuclear DNA (labeled blue with DAPI) condensation and fragmentation were observed in microinjected single cells after 5 hr incubation with wt-azurin, but not during a 30 min. incubation with azurin.

Example 9

Internalization of Wt-azurin Fusion Derivatives at 37° C.

Figure 2B:
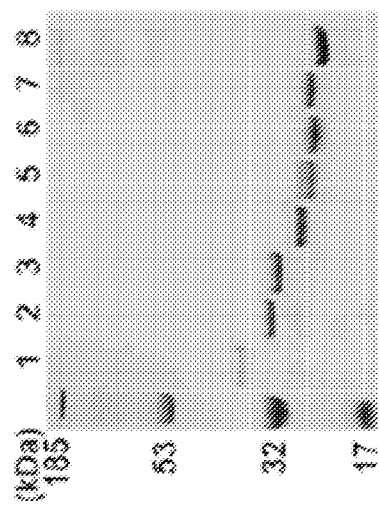
FIGS. 2(a) and (b). (a) Schematic representation of various truncated azurin constructs and their purification profiles. Various fragments of azu gene were fused at the 3'-end of the gst gene in frame. (b) GST-azu fusion proteins were purified after cellular growth and lysis, loaded on SDS-PAGE and visualized by Coomassie Blue staining.

A series of GST fusions of wt-azurin truncated at both the N- and the C-terminal were prepared and purified as in Example 1 (FIGS. 2(a) and 2(b)). Using ALEXA FLUOR® 568 conjugated wt-azurin, GST and GST-azu fusion derivatives, internalization in J774 cells at 37° C. during 1 hr incubation was examined using the method described in Example 5. The nucleus was stained blue with DAPI.

While wt-azurin was internalized, GST remained at the periphery of the cells and was not internalized. GST-azu 36-128 and GST-azu 36-89 were internalized, as was GST-azu 36-77. Further truncations, however, demonstrated that while GST-azu 50-77 was internalized, GST-azu 36-50 was highly inefficient and appeared to form clumps on the surface.

Example 10

Internalization of Azurin Fusion Derivatives at 4° C.

Internalization of wt-azurin and the GST-azu fusion derivatives in J774 cells incubated at 4° C. was examined. At 4° C., internalization of wt-azurin inside J774 cells during 1 hr incubation was severely impaired. Similar impairment was also seen with GST-azu 36-128 and GST-azu 36-89. The shorter GST-azu 36-77, GST-azu 50-77, GST-azu 50-66 and GST-azu 67-77 demonstrated severe impairment of internalization at 4° C.

Example 11

Energy-Dependent Internalization of the GST-GFP-azu 50-77 Fusion Protein in J774 and Melanoma UISO-Mel-2 Cells GST was fused with GFP to make a GST-GFP fusion derivative. Additionally, azu 50-77 was fused to the GST-GFP ($M_r$ 53 kDa) fusion protein (FIG. 3(a)). The mobility of the purified GST, GST-GFP and GST-GFP-azu 50-77 fusion derivatives was examined on SDS-PAGE (FIG. 3(b)). Detection was by Coomassie Blue staining and Western blotting using anti-azurin antibody (FIG. 3(c))

Figures 4A, 4B, 4C:
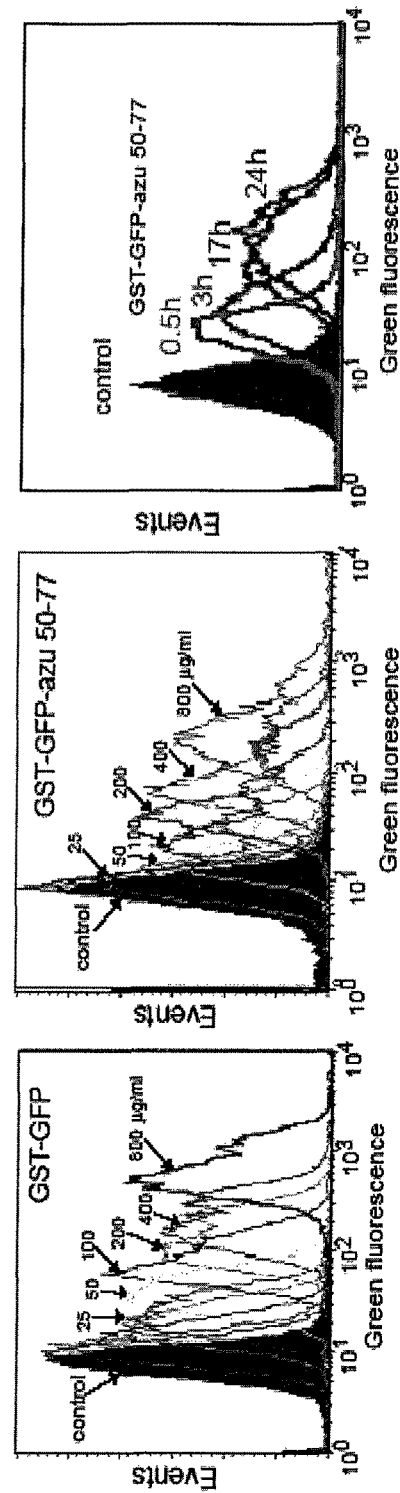
FIGS. 4(a), (b) and (c). Diagrams showing a kinetic study for the internalization of GST-Green Fluorescent Protein (GFP) and GST-GFP-azurin fusion proteins. Green fluorescence was assayed in J774 cells treated with various concentrations of GST-GFP (10(a)) or GST-GFP-azu 50-77 (10(b)) at 37° C. for 1 hr. Ten thousand cells were analyzed by flow cytometry. (c) Time-dependence of internalization of GST-GFP-azu 50-77. J774 cells were incubated with 200 µg/ml GST-GFP-azu 50-77 for indicated times at 37° C. and analyzed by flow cytometry.

Flow cytometric determination of J774 cells treated with varying concentrations of GST-GFP showed that this protein does bind to J774 cells. Flow cytometric separation of J774 cells treated with increasing concentrations of GST-GFP-azu 50-77 fusion protein demonstrated significantly reduced fluorescence than GST-GFP alone (FIG. 4). It is to be noted that internalization of GFP in mammalian cells is known to lead to loss of fluorescence. This reduction of fluorescence is also apparent when J774 cells are treated with 200 µg/ml of GST-GFP-azu 50-77 fusion protein and incubated for increasing periods of time at 37° C.

To determine if there is any difference in the binding and internalization profile of GST-GFP and GST-GFP-azu 50-77, both J774 and UISO-Mel-2 cells were incubated with GST-GFP and GST-GFP-azu 50-77 at 37° C. and at 4° C. The green fluorescence was localized using confocal microscopy. In J774 cells, GST-GFP fusion protein bound to the surface and was not internalized both at 37° C. and at 4° C. In contrast, GST-GFP-azu 50-77 was found to be internalized at 37° C., but not at 4° C. In UISO-Mel-2 cells, the GST-GFP fusion protein was retained on the surface both at 37° C. and at 4° C. In contrast, similar to J774 cells, GST-GFP-azu 50-77 fusion protein was seen to be internalized at 37° C. but not at 4° C.

Example 12

Wt-Azurin Entry into Mammalian Cells by a Cell Membrane Penetration and an Endocytic Mechanism If wt-azurin entry is solely dependent on receptor-mediated endocytosis, it could be blocked by protonophore carbonyl cyanide m-chlorophenythydrazone (CCCP), a mitochondrial uncoupler of energy generation, or preincubalion with unlabeled azurin or other cupredoxins that block the receptors. J774 and UISO-Mel-2 cells were incubated with the cupredoxins at 10 fold excess concentration for 2 hr at 4° C., the cells washed thoroughly to remove the cupredoxins, and incubated with ALEXA FLUOR® 568-conjugated azurin for 1 hr at 37° C. There was as much internalized azurin as in cells not treated with the cupredoxins. The effects of cytochalasin D (available from Sigma-Aldrich, St. Louis, Mo. 63195), a known inhibitor of receptor-mediated endocytosis that disrupts the cellular microfilament network, and Brefeldin A (available from Sigma-Aldrich, St. Louis, Mo. 63195), which is known to disrupt the Golgi apparatus and inhibit classical vesicle-mediated secretion, were also tested. CCCP at 20 pM concentration significantly reduced the uptake of azurin in UISO-MeI-2 cells as did 0.25 to 0.5 pM cytochalasin D. Brefeldin A, on the other hand, had no significant effect.

Example 13

Entry of a GST-PEDIII-azu 50-77 Fusion Derivative into UISO-Mel-2 Cells

A GST-fusion of *Pseudomonas aeruginosa* exotoxin A domain III (PEDIII) was constructed as described by Hwang, J. et al., Cell 48:129-36 (1987); Reiter, Y. and Pastan, I., Trends Biotechnol. 16:513-20 (1998). This GST-PEDIII fusion derivative contained amino acids 381-613 of the exotoxin A. PEDIII is known to harbor ADP-ribosyl transferase activity and inhibits cellular protein synthesis in eukaryotic cells by inhibiting eukaryotic elongation factor 2.

Figure 5A:
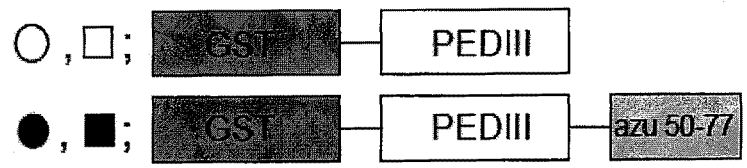
FIGS. 5(a), (b) and (c). (a) Diagram showing the exotoxin A domain III (amino acids 405-613), as well as part of domain Ib (amino acids 381-404), fused to GST (GST-PEDIII) as earlier described for the GST-GFP fusion. The azu 50-77 fragment was then ligated to the carboxyl end of GST-PEDIII (GST-PEDIII-azu 50-77), using PCR. (b) The fusion proteins were purified by glutathione Sepharose 4B column gel filtration column chromatography and run on SDS-PAGE for size determination. (c) Diagram showing action of GST-PEDIII-azu 50-77 fusion protein in UISO-Mel-2 cancer cells and in normal fibroblast (FBT) cells, as determined by PEDIII-mediated cytotoxicity. Various concentrations, as indicated, of GST-PEDIII and GST-PEDIII-azu 50-77 were incubated with UISO-Mel-2 and FBT cells for 24 h, after which the cell viability was determined by MTT assay.
Figure 5B:
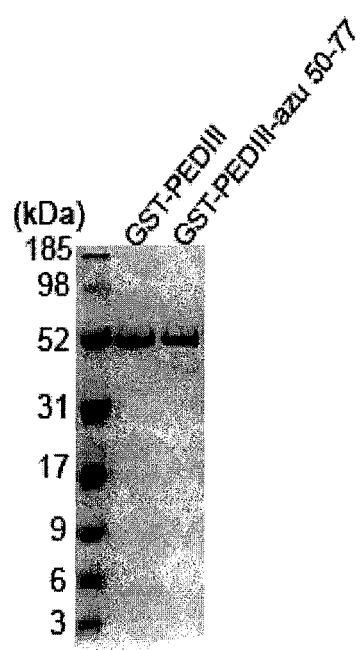

Using PCR as described for the GST-GFP-azu 50-77, the azu 50-77 sequence was introduced to the carboxyl end of the GST-PEDIII fusion protein (FIG. 5(a)). These two fusion proteins (GSTPEDIII and GST-PEDIII-azu 50-77) were purified by glutathione-sepharose 4B column chromatography as 52 and 54 kDa proteins (FIG. 5(b)). UISO-Mel-2 and normal fibroblast (FBT) cells were then incubated for 24 h at 37° C. with various concentrations of these proteins and the extent of cell death measured by MTT assay as described in Example 7.

Figure 5C:
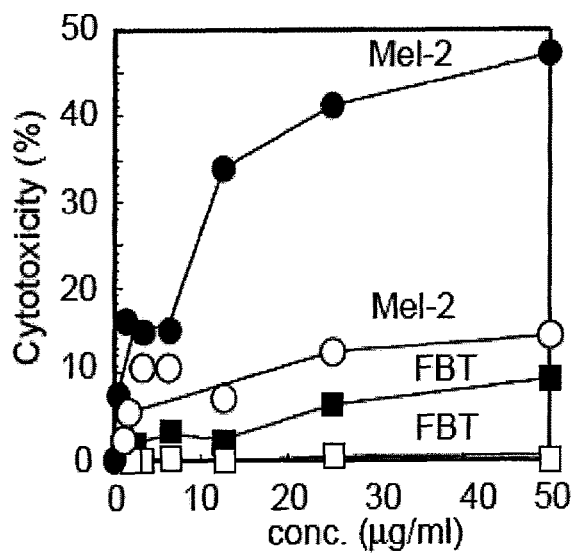

While GST-PEDIII demonstrated only low cytotoxicity, the GST-PEDIII-azu 50-77 fusion protein had high cytotoxicity because of efficient entry to UISO-Mel-2 cells (FIG. 5(c)). In contrast, the fusion proteins demonstrated a low level of cytotoxicity towards the fibroblast cells.

Example 14

Figure 6:
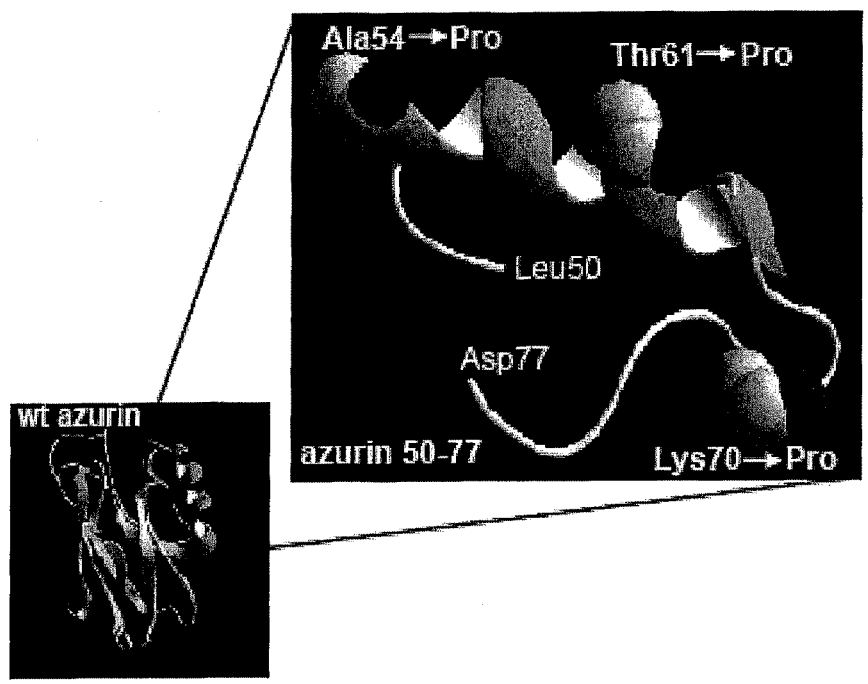
FIG. 6. Diagram showing the localization of the α-helix in wt-azurin as well as in the wt-azurin 50-77 protein transduction domain. Replacement of three amino acids in the azurin 50-77 domain by proline residues is indicated.

Destabilization of the α-Helix in wt-Azurin has no Substantial Effect on its Internalization in UISO-Mel-2 Cells To examine if the α-helix plays a role in azurin entry, three helix-destabilizing proline residues were introduced in positions 54, 61 and 70 of wt-azurin (FIG. 6) and examined the entry of the full length A54PT61PK70P mutant azurin into UISO-Mel-2 cells. Single and double mutations in these positions were also constructed and tested for entry. The A54PT61PK70P mutant azurin was prepared by site-directed mutagenesis of the azurin gene using the QuickChange site-directed mutagenesis kit (Stratagene, La Jolla, Calif.).

The mutants were incubated at 200 µg/ml with UISO-Mel-2 cells for 1 hr at 37° C., after which the fluorescence was localized by confocal microscopy. In all cases, the ALEXA FLUOR® 568-conjugated mutant azurins entered UISO-Mel-2 cells. Similarly, when the GST-GFP-azu 50-77 fusion protein, as well as its triple A54PT61PK70P azu mutant variant, were examined for entry in UISO-Mel-2 cells, no significant difference was observed.

Example 15

Entry of a GST-PEDIII-Rusticyanin Fusion Derivative into UISO-Mel-2 Cells

A GST-fusion of Pseudomonas aeruginosa exotoxin A domain III (PEDIII) and was constructed as in Example 13. Using PCR as described for the GST-GFP-azu 50-77, full-length rusticyanin sequence was introduced to the carboxyl end of the GST-PEDIII fusion protein. The fusion protein was purified by glutathione-sepharose 4B column chromatography. UISO-Mel-2 and FBT cells were then incubated for 24 h at 37° C. with various concentrations of the fusion protein and the extent of cell death measured by MTT assays as described in Example 7.

Figure 7:
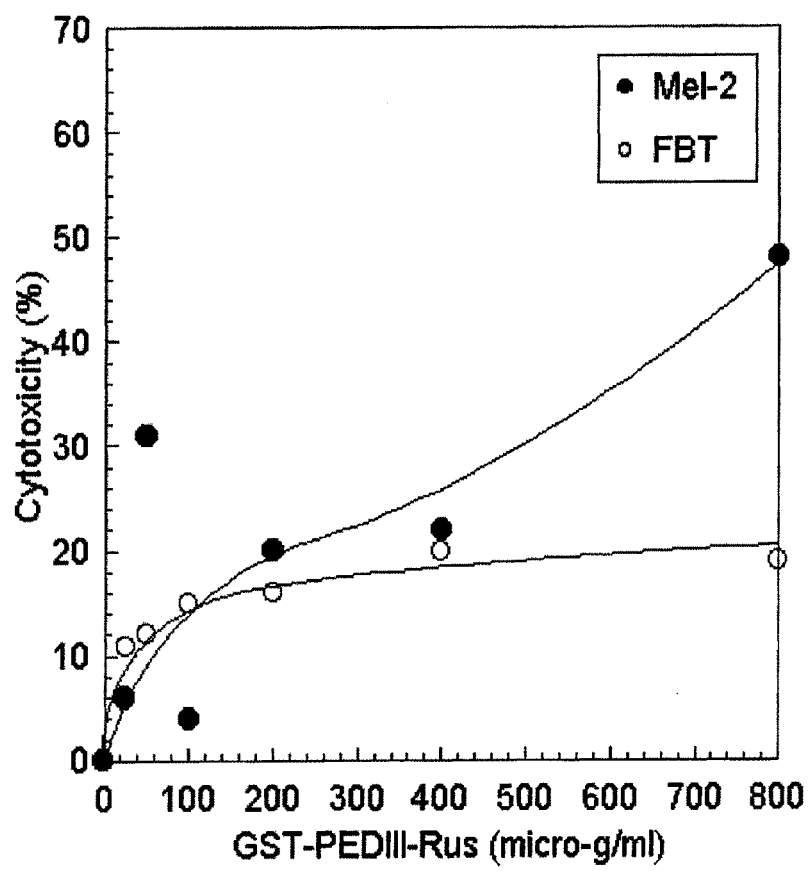
FIG. 7. Diagram PEDIII-mediated cytotoxicity of GST-PEDIII-rusticyanin fusion protein against UISO-Mel-2 cancer cells and FBT cells. Various concentrations, as indicated, of GST-PEDIII and GST-PEDIII-azu 50-77 were incubated with UISO-Mel-2 and FBT cells for 24 h, after which the cell viability was determined by MTT assay.

The GST-PEDIII-rusticyanin fusion protein exhibited high cytotoxicity against UISO-Mel-2 cells (FIG. 7). In contrast, the fusion protein demonstrated only a low level of cytotoxicity towards the FBT cells.

Example 16

Competition of Azurin with GST-Azu 55-77 for Entry into J774 Cells

A competition experiment was performed with unlabeled azurin at 37° C. in presence of 7 µM Alexa Fluor®-conjugated GST-azu 50-77. J774 cells were incubated without Alexa Fluor®-conjugated azurin, with Alexa Fluor®-conjugated GST-azu 50-77 (7 µM) and with Alexa fluor-conjugated GST-azu 50-77 (7 µM) in presence of 7, 14 and 56 µM of unlabeled azurin for 1 h at 37° C. before determining GST-azu 50-77 entry. The results clearly demonstrated that in comparison to labeled 7 µM GST-azu 50-77 alone, the presence of increasing amounts of unlabeled azurin (7, 14 and 56 µM) increasingly competed with the entry of labeled 7 µM GST-azu 50-77. In contrast, when similar concentrations of (6, 12 and 48 µM) unlabeled rusticyanin were used in presence of labeled GST-azu 50-77, very little effect on the entry of GST-azu 50-77 was seen.

Example 17

Figures 8A, 8B:
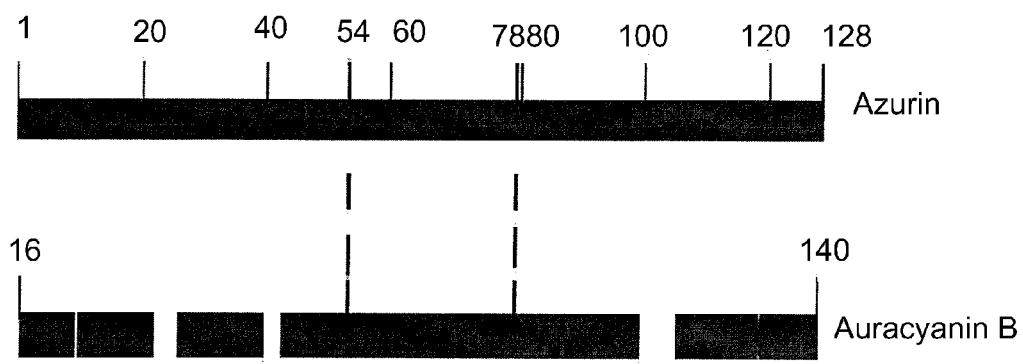
FIGS. 8(a) and (b). (a) Diagram showing the structural alignment of azurin with other cupredoxins, as computed by the VAST algorithm. The N-terminal extended parts of auracyanin B and rusticyanin, being absent in azurin, have been omitted in the figure. The gray bars indicate the regions of azurin that can be superimposed on residues from each neighbor. The blank spaces are unaligned regions. The azurin protein transduction domain (PTD), azurin amino acids 50-77, where there is no alignment with rusticyanin is highlighted by vertical dashed lines. The numbers in parentheses after the names of the cupredoxins are the protein database accession numbers. (b). Multiple amino acid sequence alignment of the residues comprising the middle part in some known bacterial azurins. Bacterial genus and species are abbreviated as follows: Psae, *Pseudomonas aeruginosa* (SEQ ID NO:44); Pssy, *Pseudomonas syringae* (SEQ ID NO: 45); Neme, *Neisseria meningitidis* (SEQ ID NO:40); Vipa, *Vibrio parahaemolyticus* (SEQ ID NO:46); Bobr, *Bordetella bronchiseptica* (SEQ ID NO:47). Numbers of intervening amino acids are given in parenthesis. The CLUSTAL X software (Higgins and Sharp, *Gene* 101:6427-6432 (1988)) was used to generate this multiple sequence alignment.
Figure 9:
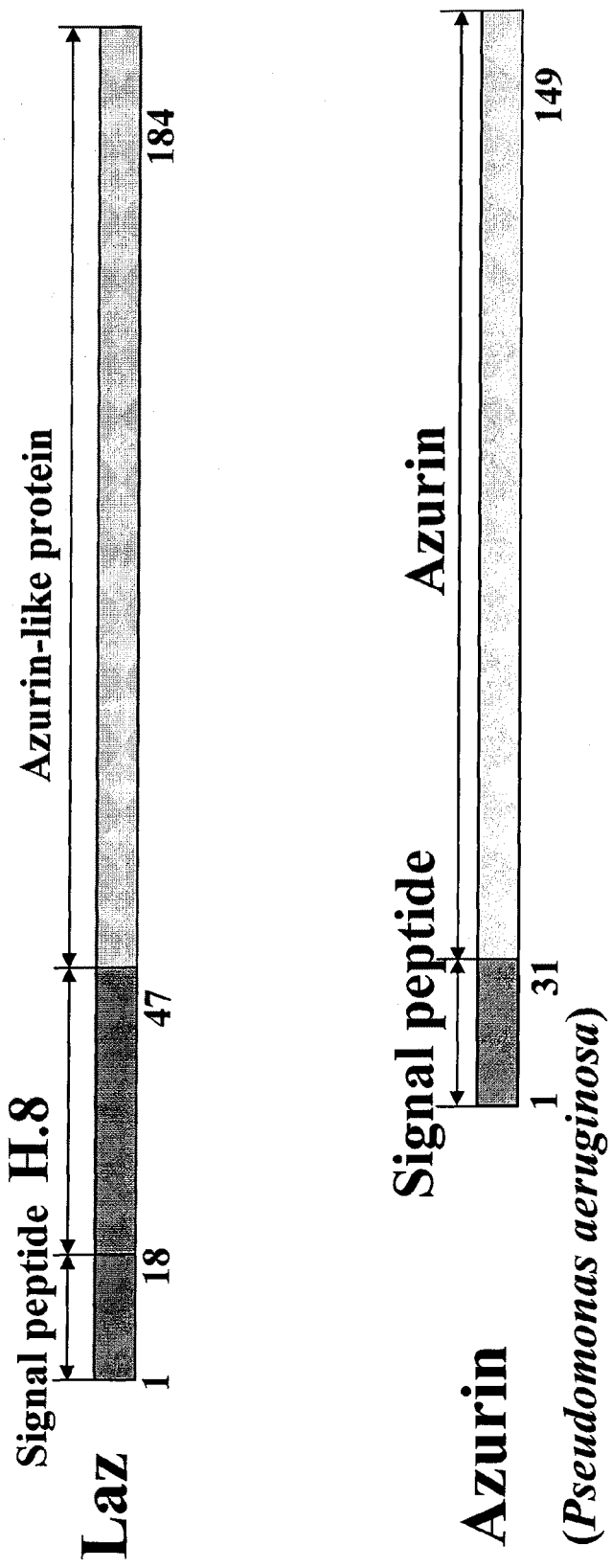
FIG. 9.

Sequence and Structural Comparison of Azurin Protein Transduction Domain (PTD) with other Cupredoxins The sequence identity between azurin and rusticyanin in the azu 50-77 region is less than 20%, as is true of several other cupredoxins (De Rienzo et al., Protein Science 9:1439-1454, 2000; Murphy et al., J. Mol. Biol. 315:859-871, 2002). A structural analysis using VAST algorithm (Gibrat et al., Curr. Opin. Struct. Biol. 6:377-385, 1996) between azurin and several members of the cupredoxin family demonstrated a significant identity between azu 50-77 region and that of the cupredoxin auracyanin B, a cupredoxin from the green thermophilic photosynthetic bacterium C. aurantiacus (Bond et al., J. Mol. Biol. 306:47-67, 2001). Other members of the cupredoxin family, while demonstrating structural similarity with other regions of azurin lacked significant identity with the azurin PTD, amino acids 50-77 (FIG. 8(a)). Indeed, when compared with other proteins whose structures have been deposited in the protein database, there was very little structural similarity between the azu PTD and other proteins.

A multiple amino acid sequence alignment of the residues in the P. aeruginosa PTD region with known sequences of other bacterial azurins from pathogens using the CLUSTAL X alignment program (Higgins and Sharp, id. 1988). While the phytopathogenic P. syringae azurin showed high identity with P. aeruginosa azurin PTD region, an azurin-like protein from Neisseria meningitidis (Gotschlich and Seiff, FEMS Microbiol. Lett. 43:253-255 (1987); Kawula et al., Mol. Microbiol. 1:179-185 (1987); Cannon, Clin. Microbiol. Rev. 2:S1-S4 (1989)) also showed significant identity with the PTD domain of P. aeruginosa azurin, as did azurins from Vibrio parahaemolyticus and Bordetella bronchiseptica (FIG. 8(b)). A motif sequence D-G-X-X-X-X-X-D-X-X-Y-X-K-X-X-D (SEQ ID NO: 35) was found conserved in all these azurins.

Example 18

N. meningitidis Laz (H8-Azurin) Induces cell Death in the Brain Tumor cell Line LH229

Neisseria meningitidis (Nm) causes cerebrospinal meningitis by disseminating in the blood stream, crossing the blood brain barrier, presumably by a transcellular route through brain endothelial cells, and invading the meninges. The azurins from both Pseudomonas aeruginosa and Neisseria meningitidis have similar structures and high amino acid sequence homology (>50%). In addition, the N. meningitidis azurin is part of a longer polypeptide, Laz (SEQ ID NO: 30), which harbors in its N-terminal a surface peptide called H.8, which is present in the outer membrane of N. meningitidis (Cannon, J. G., Clin. Microbiol. Rev. vol. 2, pp. 51-54 (1989)). The surface-exposed H8 antigenic epitope at also carries a signal for lipidation. The complete N. meningitidis H8 outer membrane protein remains on the external surface of N. meningitidis cells.

The Neisseria gonorrhoeae Laz protein is very similar to the N. meningitidis Laz protein. The N. gonorrhoeae laz gene was cloned into E. coli, and then the laz gene in the E. coli was hyper-expressed to produce the Laz protein (FIG. 13). The ability of the purified P. aeruginosa azurin and the purified N. gonorrhoeae Laz protein to induce cell death in the brain tumor cell line LH229 as measured by the MTT assay (Yamada, T., et al., Cell Cycle vol. 3, pp. 1182-1187 (2004)).

While P. aeruginosa azurin, when expressed in E. coli, is present in the periplasm, the Laz protein, when expressed in E. coli, was found in the outer membrane of E. coli. Additionally, while azurin had very low cytotoxicity towards the brain tumor cells within 24 hours, Laz showed high cytotoxicity, allowing the death of 90% of the brain tumor cells in 24 hours (Table 3). Azurin did show increasing cytotoxicity over 48 hours (Table 4). This experiment indicates that P. aeruginosa azurin and the N. gonorrhoeae H8-azurin (Laz, SEQ ID NO: 36) will be useful to diagnose and/or treat brain tumors in vitro and in vivo.

If Laz reduces brain tumor growth in vivo, all or part of the protein will be used as the "cupredoxin entry domain" of the invention to transport cargo molecules, including fluorescent or radioactive tags or tumor-killing drugs/toxins, into the brain, and into brain tumor cells for diagnostic or therapeutic purposes.

TABLE 3

Cytotoxicity of P. aeruginosa azurin and N. gonorrhoeae Laz to Brain Cancer Cell Line LH229 After 24 Hours Incubation.

| Protein | Conc. | Cytotoxicity (%) | STDEV |
| --- | --- | --- | --- |
| P. aeruginosa azurin | 0 | 0.00 | 0.00 |
| N. gonorrhoeae Laz | 0 | 0.00 | 0.00 |
| P. aeruginosa azurin | 25 | 5.86 | 2.45 |
| N. gonorrhoeae Laz | 25 | 18.80 | 1.26 |
| P. aeruginosa azurin | 50 | 5.48 | 2.43 |
| N. gonorrhoeae Laz | 50 | 23.59 | 1.57 |
| P. aeruginosa azurin | 100 | 6.00 | 4.13 |
| N. gonorrhoeae Laz | 100 | 41.02 | 1.49 |
| P. aeruginosa azurin | 200 | 8.27 | 4.79 |
| N. gonorrhoeae Laz | 200 | 78.99 | 2.06 |
| P. aeruginosa azurin | 400 | 7.25 | 3.69 |
| N. gonorrhoeae Laz | 400 | 94.69 | 0.87 |
| P. aeruginosa azurin | 800 | 13.22 | 7.67 |
| N. gonorrhoeae Laz | 800 | 98.36 | 0.62 |

TABLE 4

Cytotoxicity of *P. aeruginosa* azurin and *N. gonorrhoeae* Laz to Brain Cancer Cell Line LH229 After 48 Hours of Incubation.

| Protein | Conc. (μg/ml) | Cytotoxicity (%) | STDEV |
|---|---|---|---|
| *P. aeruginosa* azurin | 0 | 0.00 | 0.00 |
| *N. gonorrhoeae* Laz | 0 | 0.00 | 0.00 |
| *P. aeruginosa* azurin | 25 | 11.65 | 1.07 |
| *N. gonorrhoeae* Laz | 25 | 20.04 | 4.25 |
| *P. aeruginosa* azurin | 50 | 8.55 | 2.51 |
| *N. gonorrhoeae* Laz | 50 | 25.52 | 1.80 |
| *P. aeruginosa* azurin | 100 | 16.19 | 2.60 |
| *N. gonorrhoeae* Laz | 100 | 39.72 | 0.92 |
| *P. aeruginosa* azurin | 200 | 16.30 | 1.91 |
| *N. gonorrhoeae* Laz | 200 | 87.01 | 1.21 |
| *P. aeruginosa* azurin | 400 | 61.96 | 19.15 |
| *N. gonorrhoeae* Laz | 400 | 98.75 | 0.96 |
| *P. aeruginosa* azurin | 800 | 82.71 | 5.91 |
| *N. gonorrhoeae* Laz | 800 | 99.93 | 0.12 |

Example 19

Cytotoxicity of the *N. gonorrhoeae* Laz Protein to Brain Tumor Cells

Figure 10:
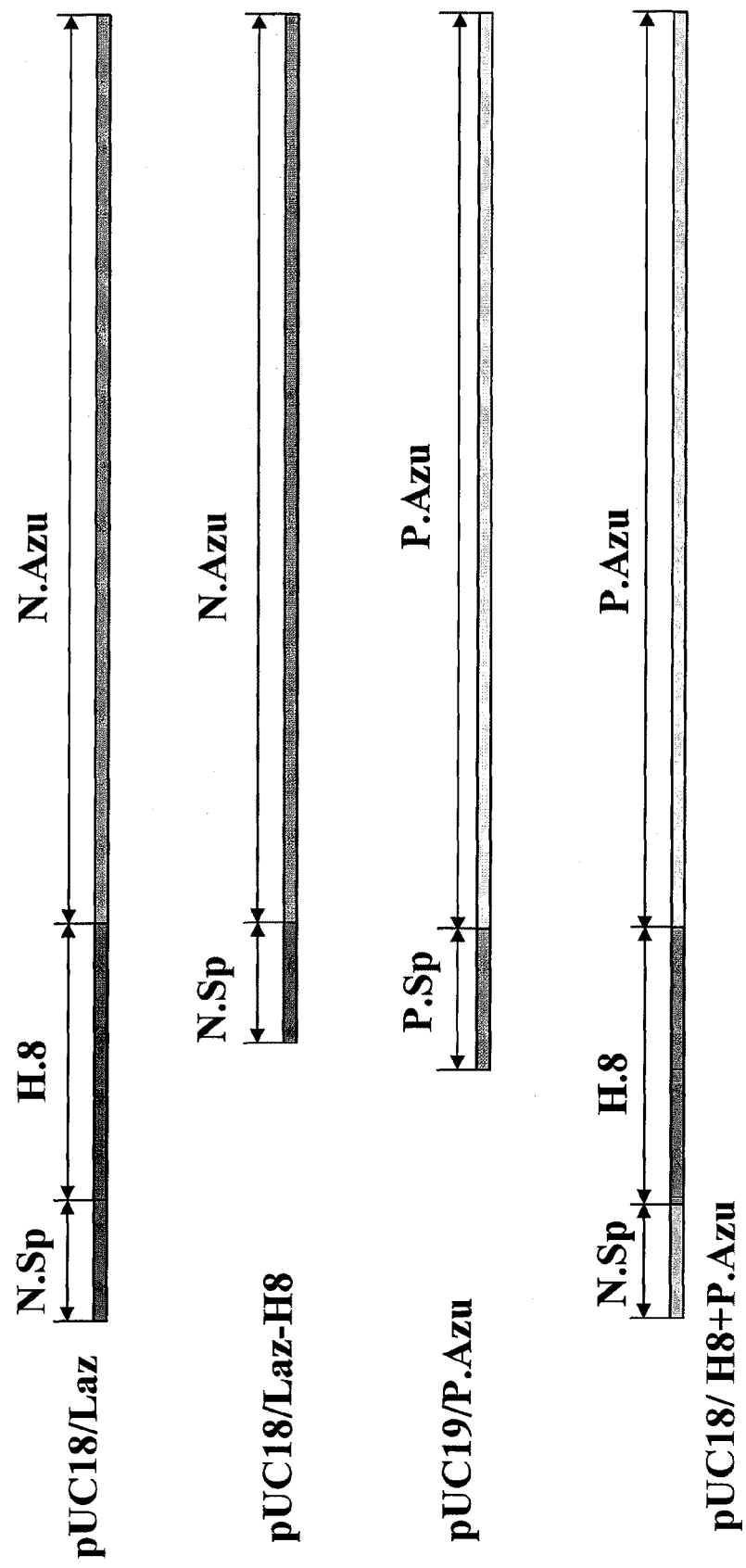
FIG. 10.

Several plasmids were constructed encoding protein constructs including *P. aeruginosa* azurin, *N. gonorrhoeae* Laz (SEQ ID NO:36), and fusion proteins, and the proteins tested in the MTT assay with brain tumor cell lines. The protein constructs tested include the *N. gonorrhoeae* Laz H.8 region alone, *P. aeruginosa* azurin alone, *N. gonorrhoeae* azurin alone, and the constructs depicted in FIG. 10. The plasmids encoding the protein constructs are transformed into *E. coli* or another suitable expression system, and the protein constructs expressed and the resulting proteins purified. Brain tumor cell lines include NL229 and CCF-STTG1.

The results of this experiment indicate that the H.8 region and/or the azurin of the Laz gene are required to allow the protein construct to be cytotoxic to brain tumor cells. This experiment also determines if other azurins will be more cytotoxic to brain tumor cells if fused to the H.8 region. The results of this experiment indicate that the H.8 region can adapt a cupredoxin to be cytotoxic to brain cancer cell by transporting the attached azurin into the brain cancer cells. Accordingly, H.8 can be used as a transport domain to transport a cargo molecule(s) into brain cancer cells. Useful cargos include cancer treatments and diagnostic agents as known in the art and set forth herein.

Example 20

Treatment of Patients Suffering from Cancer

A Phase I/II clinical trial of a cupredoxin entry domain-exotoxin A domain III fusion (Study Drug) will be performed in patients suffering from cancer. Specifically, the cupredoxin entry domain is the 50-67 amino acid region from *Pseudomonas aeruginosa* and the cargo is the exotoxin A domain III from *Pseudomonas aeruginosa*, making the fusion protein "PEDIII-azu 50-67." This fusion protein will be constructed as illustrated in Example 13.

Forty-nine adult patients with histologically verified cancers of the breast, colon and melanoma who demonstrate clinical and radiographic progression or recurrence following adequate treatment by currently available FDA-approved chemotherapeutic drugs and regimen will be enrolled in an open-label prospective study administering the Study Drug. To be eligible for enrollment in the study, all patients demonstrate increasing volume of measurable tumor after completion of approved course of chemotherapy regimens. The evidence of persistent metastatic deposits and/or continued increase in size or volume must be histologically established. This histological proof can be obtained by a fine needle aspiration (FNA) biopsy.

The treatment program will be instituted after obtaining informed consent from all patients in accordance with the Institutional Review Board of the University of Illinois, Chicago and the FDA. The patients will have no intercurrent illness such as other malignancy, history of previous malignancy, blood dyscrasias, insulin dependent diabetes or other serious cardiovascular diseases which might interfere in appropriate evaluation of the effects of the proposed therapy. Baseline blood work (Complete Blood Counts [CBC] and Serum Chemistry) including liver function studies (LFT) will be performed prior to initiation of therapy. All eligible patients must not receive any cancer chemotherapy concurrently during the period of the trial.

The study drug(s) will be administered by daily intravenous injection of a pharmaceutically acceptable preparation of the Study Drug for 12 weeks and the subjects will be observed for any dose limiting toxicity. There will be 7 dose levels starting with 10 mg/kg/day and increasing by 5 mg/kg/day up to a maximum dose of 50 mg/kg/day. The efficacy of each dose level will be recorded in 7 patients with advanced measurable cancer (breast, colon, and melanoma).

The response will be estimated by measuring the measurable tumor in 2 dimensions (a and b). 1) Total disappearance of the target metastatic tumors will be considered as complete response (CR); 2) A 75% reduction will be considered excellent, partial response (PR); and 3) A good response (PR) will be post treatment reduction in size by 50%. 4) Reduction of 25% in size will be considered as stable disease (SD) and 5) <25% will be considered as no response (NR). Patients demonstrating a progression of disease will have their treatment discontinued but will be followed for an additional 12 weeks.

Total disappearance, and any reduction in size of the target metastatic tumors will indicate that the azurin treatment is effective for treating cancer. Other indications that the azurin treatment is effective are a decrease rate of in the appearance of new metastatic tumors and a decrease in the angiogenesis associated with tumors.

Various modifications and variations of the described examples and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in related fields are intended to be within the scope of the following claims.

SEQUENCE LISTING

<160> NUMBER OF SEQ ID NOS: 48

<210> SEQ ID NO 1
<211> LENGTH: 128

```
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 105
<212> TYPE: PRT
<213> ORGANISM: Phormidium laminosum

<400> SEQUENCE: 2

Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
            35                  40                  45

Pro Gly Ala Ser Lys Glu Leu Ala Asp Lys Leu Ser His Ser Gln Leu
    50                  55                  60

Met Phe Ser Pro Gly Glu Ser Tyr Glu Ile Thr Phe Ser Ser Asp Phe
65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105

<210> SEQ ID NO 3
<211> LENGTH: 155
<212> TYPE: PRT
<213> ORGANISM: Thiobacillus ferrooxidans

<400> SEQUENCE: 3

Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
            20                  25                  30

Tyr Ser Gly Lys Thr Val His Val Val Ala Ala Val Leu Pro Gly
        35                  40                  45

Phe Pro Phe Pro Ser Phe Glu Val His Asp Lys Lys Asn Pro Thr Leu
    50                  55                  60

Glu Ile Pro Ala Gly Ala Thr Val Asp Val Thr Phe Ile Asn Thr Asn
65                  70                  75                  80
```

```
Lys Gly Phe Gly His Ser Phe Asp Ile Thr Lys Lys Gly Pro Pro Tyr
                    85                  90                  95

Ala Val Met Pro Val Ile Asp Pro Ile Val Ala Gly Thr Gly Phe Ser
            100                 105                 110

Pro Val Pro Lys Asp Gly Lys Phe Gly Tyr Thr Asp Phe Thr Trp His
            115                 120                 125

Pro Thr Ala Gly Thr Tyr Tyr Tyr Val Cys Gln Ile Pro Gly His Ala
        130                 135                 140

Ala Thr Gly Met Phe Gly Lys Ile Val Val Lys
145                 150                 155

<210> SEQ ID NO 4
<211> LENGTH: 124
<212> TYPE: PRT
<213> ORGANISM: Achromabacter cycloclastes

<400> SEQUENCE: 4

Ala Asp Phe Glu Val His Met Leu Asn Lys Gly Lys Asp Gly Ala Met
1               5                   10                  15

Val Phe Glu Pro Ala Ser Leu Lys Val Ala Pro Gly Asp Thr Val Thr
                20                  25                  30

Phe Ile Pro Thr Asp Lys Gly His Asn Val Glu Thr Ile Lys Gly Met
            35                  40                  45

Ile Pro Asp Gly Ala Glu Ala Phe Lys Ser Lys Ile Asn Glu Asn Tyr
        50                  55                  60

Lys Val Thr Phe Thr Ala Pro Gly Val Tyr Gly Val Lys Cys Thr Pro
65                  70                  75                  80

His Tyr Gly Met Gly Met Val Gly Val Val Gln Val Gly Asp Ala Pro
                85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
        115                 120

<210> SEQ ID NO 5
<211> LENGTH: 93
<212> TYPE: PRT
<213> ORGANISM: Pseudomonas aeruginosa

<400> SEQUENCE: 5

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
                20                  25                  30

Leu Asp Lys Asp Tyr Leu Lys Pro Asp Asp Ser Arg Val Ile Ala His
            35                  40                  45

Thr Lys Leu Ile Gly Ser Gly Glu Lys Asp Ser Val Thr Phe Asp Val
        50                  55                  60

Ser Lys Leu Lys Glu Gly Glu Gln Tyr Met Phe Phe Cys Thr Phe Pro
65                  70                  75                  80

Gly His Ser Ala Leu Met Lys Gly Thr Leu Thr Leu Lys
                85                  90

<210> SEQ ID NO 6
<211> LENGTH: 54
<212> TYPE: PRT
<213> ORGANISM: Pseudomonas aeruginosa
```

```
<400> SEQUENCE: 6

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly Ser
    50

<210> SEQ ID NO 7
<211> LENGTH: 42
<212> TYPE: PRT
<213> ORGANISM: Pseudomonas aeruginosa

<400> SEQUENCE: 7

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp
        35                  40

<210> SEQ ID NO 8
<211> LENGTH: 15
<212> TYPE: PRT
<213> ORGANISM: Pseudomonas aeruginosa

<400> SEQUENCE: 8

Pro Gly Asn Leu Pro Lys Asn Val Met Gly His Asn Trp Val Leu
1               5                   10                  15

<210> SEQ ID NO 9
<211> LENGTH: 28
<212> TYPE: PRT
<213> ORGANISM: Pseudomonas aeruginosa

<400> SEQUENCE: 9

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 10
<211> LENGTH: 17
<212> TYPE: PRT
<213> ORGANISM: Pseudomonas aeruginosa

<400> SEQUENCE: 10

Leu Ser Thr Ala Ala Asp Met Gln Gly Val Val Thr Asp Gly Met Ala
1               5                   10                  15

Ser

<210> SEQ ID NO 11
<211> LENGTH: 11
<212> TYPE: PRT
<213> ORGANISM: Pseudomonas aeruginosa

<400> SEQUENCE: 11

Gly Leu Asp Lys Asp Tyr Leu Lys Pro Asp Asp
1               5                   10
```

```
<210> SEQ ID NO 12
<211> LENGTH: 37
<212> TYPE: DNA
<213> ORGANISM: Artificial sequence
<220> FEATURE:
<223> OTHER INFORMATION: forward primer for pGST-azu 36-128

<400> SEQUENCE: 12
cgggatcccc ggcaacctgc cgaagaacgt catgggc                              37

<210> SEQ ID NO 13
<211> LENGTH: 28
<212> TYPE: DNA
<213> ORGANISM: Artificial sequence
<220> FEATURE:
<223> OTHER INFORMATION: reverse primer for pGST-azu 36-128

<400> SEQUENCE: 13
cggaattcgc atcacttcag ggtcaggg                                         28

<210> SEQ ID NO 14
<211> LENGTH: 39
<212> TYPE: DNA
<213> ORGANISM: Artificial sequence
<220> FEATURE:
<223> OTHER INFORMATION: forward oligonucleotide for pGST-azu 36-50

<400> SEQUENCE: 14
ggccacaact gggtactgtg aaccgccgcc gacatgcag                             39

<210> SEQ ID NO 15
<211> LENGTH: 39
<212> TYPE: DNA
<213> ORGANISM: Artificial sequence
<220> FEATURE:
<223> OTHER INFORMATION: reverse oligonucleotide for pGST-azu 36-50

<400> SEQUENCE: 15
ctgcatgtcg gcggcggttc acagtaccca gttgtggcc                             39

<210> SEQ ID NO 16
<211> LENGTH: 37
<212> TYPE: DNA
<213> ORGANISM: Artificial sequence
<220> FEATURE:
<223> OTHER INFORMATION: forward oligonucleotide for pGST-azu 36-77

<400> SEQUENCE: 16
cctgaagccc gacgactgac gtgtcatcgc ccacacc                               37

<210> SEQ ID NO 17
<211> LENGTH: 37
<212> TYPE: DNA
<213> ORGANISM: Artificial sequence
<220> FEATURE:
<223> OTHER INFORMATION: reverse oligonucleotide for pGST-azu 36-77

<400> SEQUENCE: 17
ggtgtgggcg atgacacgtc agtcgtcggg cttcagg                               37

<210> SEQ ID NO 18
<211> LENGTH: 38
<212> TYPE: DNA
<213> ORGANISM: Artificial sequence
<220> FEATURE:
<223> OTHER INFORMATION: forward oligonucleotide for pGST-azu 36-89
```

```
<400> SEQUENCE: 18
ccaagctgat cggctcgtga gagaaggact cggtgacc                              38

<210> SEQ ID NO 19
<211> LENGTH: 38
<212> TYPE: DNA
<213> ORGANISM: Artificial sequence
<220> FEATURE:
<223> OTHER INFORMATION: reverse oligonucleotide for pGST-azu 36-89

<400> SEQUENCE: 19
ggtcaccgag tccttctctc acgagccgat cagcttgg                              38

<210> SEQ ID NO 20
<211> LENGTH: 33
<212> TYPE: DNA
<213> ORGANISM: Artificial sequence
<220> FEATURE:
<223> OTHER INFORMATION: forward primer for pGST-azu 50-77

<400> SEQUENCE: 20
cgggatcctg agcaccgccg ccgacatgca ggg                                   33

<210> SEQ ID NO 21
<211> LENGTH: 38
<212> TYPE: DNA
<213> ORGANISM: Artificial sequence
<220> FEATURE:
<223> OTHER INFORMATION: forward primer for pGST-azu 67-77

<400> SEQUENCE: 21
cgggatcccc ggcctggaca aggattacct gaagcccg                              38

<210> SEQ ID NO 22
<211> LENGTH: 28
<212> TYPE: DNA
<213> ORGANISM: Artificial sequence
<220> FEATURE:
<223> OTHER INFORMATION: reverse primer for pGST-azu 50-77 and
      pGST-azu 67-77

<400> SEQUENCE: 22
cggaattcgc atcacttcag ggtcaggg                                         28

<210> SEQ ID NO 23
<211> LENGTH: 34
<212> TYPE: DNA
<213> ORGANISM: Artificial sequence
<220> FEATURE:
<223> OTHER INFORMATION: forward oligonucleotide for pGST-azu 50-66

<400> SEQUENCE: 23
gacggcatgg cttcctgact ggacaaggat tacc                                  34

<210> SEQ ID NO 24
<211> LENGTH: 34
<212> TYPE: DNA
<213> ORGANISM: Artificial sequence
<220> FEATURE:
<223> OTHER INFORMATION: reverse oligonucleotide for pGST-azu 50-66

<400> SEQUENCE: 24
ggtaatcctt gtccagtcag gaagccatgc cgtc                                  34

<210> SEQ ID NO 25
<211> LENGTH: 26
```

```
<212> TYPE: DNA
<213> ORGANISM: Artificial sequence
<220> FEATURE:
<223> OTHER INFORMATION: forward primer for green fluorescence protein
      gene

<400> SEQUENCE: 25
cgggatcccc atggtgagca agggcg                                          26

<210> SEQ ID NO 26
<211> LENGTH: 30
<212> TYPE: DNA
<213> ORGANISM: Artificial sequence
<220> FEATURE:
<223> OTHER INFORMATION: reverse primer for green fluoresence protein
      gene

<400> SEQUENCE: 26
cggaattcct tgtacagctc gtccatgccg                                      30

<210> SEQ ID NO 27
<211> LENGTH: 33
<212> TYPE: DNA
<213> ORGANISM: Artificial sequence
<220> FEATURE:
<223> OTHER INFORMATION: forward primer for gst-gfp-azu 50-77

<400> SEQUENCE: 27
ccgctcgagc ctgagcaccg ccgccatgca ggg                                  33

<210> SEQ ID NO 28
<211> LENGTH: 43
<212> TYPE: DNA
<213> ORGANISM: Artificial sequence
<220> FEATURE:
<223> OTHER INFORMATION: reverse primer for gst-gfp-azu 50-77

<400> SEQUENCE: 28
ttttcctttt gcggccgctc agtcgtcggg cttcaggtaa tcc                       43

<210> SEQ ID NO 29
<211> LENGTH: 136
<212> TYPE: PRT
<213> ORGANISM: Pseudomonas syringae

<400> SEQUENCE: 29

Met Ala Ser Gly Gln Leu Leu Ala Ala Glu Cys Ser Ala Thr Val Asp
1               5                   10                  15

Ser Thr Asp Gln Met Met Tyr Asp Thr Lys Ala Ile Gln Ile Asp Lys
            20                  25                  30

Ser Cys Lys Glu Phe Thr Leu Asn Leu Thr His Ser Gly Ser Leu Pro
        35                  40                  45

Lys Asn Val Met Gly His Asn Trp Val Leu Ser Lys Lys Ala Asp Ala
    50                  55                  60

Ser Ala Ile Thr Thr Asp Gly Met Ser Val Gly Ile Asp Lys Asp Tyr
65                  70                  75                  80

Val Lys Pro Asp Asp Thr Arg Val Ile Ala His Thr Lys Ile Ile Gly
                85                  90                  95

Ala Gly Glu Asn Asp Ser Val Thr Phe Asp Val Ser Lys Leu Asp Pro
            100                 105                 110

Ala Glu Asp Tyr Gln Phe Phe Cys Thr Phe Pro Gly His Ile Ser Met
        115                 120                 125

Met Lys Gly Ala Val Thr Leu Lys
    130                 135
```

130                 135

<210> SEQ ID NO 30
<211> LENGTH: 183
<212> TYPE: PRT
<213> ORGANISM: Neisseria meningitidis

<400> SEQUENCE: 30

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
                20                  25                  30

Ala Glu Ala Pro Ala Ser Glu Ala Pro Ala Ala Glu Ala Ala Pro Ala
            35                  40                  45

Asp Ala Ala Glu Ala Pro Ala Ala Gly Asn Cys Ala Ala Thr Val Glu
        50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Thr Ser Met Gly His Asn Ile Val Ile Gly Lys Thr Glu Asp Met
                100                 105                 110

Asp Gly Ile Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 31
<211> LENGTH: 150
<212> TYPE: PRT
<213> ORGANISM: Vibrio parahaemolyticus

<400> SEQUENCE: 31

Met Ser Leu Arg Ile Leu Ala Ala Thr Leu Ala Leu Ala Gly Leu Ser
1               5                   10                  15

Phe Gly Ala Gln Ala Ser Ala Glu Cys Glu Val Ser Ile Asp Ala Asn
                20                  25                  30

Asp Met Met Gln Phe Ser Thr Lys Thr Leu Ser Val Pro Ala Thr Cys
            35                  40                  45

Lys Glu Val Thr Leu Thr Leu Asn His Thr Gly Lys Met Pro Ala Gln
        50                  55                  60

Ser Met Gly His Asn Val Val Ile Ala Asp Thr Ala Asn Ile Gln Ala
65                  70                  75                  80

Val Gly Thr Asp Gly Met Ser Ala Gly Ala Asp Asn Ser Tyr Val Lys
                85                  90                  95

Pro Asp Asp Glu Arg Val Tyr Ala His Thr Lys Val Val Gly Gly Gly
                100                 105                 110

Glu Ser Thr Ser Ile Thr Phe Ser Thr Glu Lys Met Thr Ala Gly Gly
            115                 120                 125

Asp Tyr Ser Phe Phe Cys Ser Phe Pro Gly His Trp Ala Ile Met Gln
        130                 135                 140

```
Gly Lys Phe Glu Phe Lys
145                 150

<210> SEQ ID NO 32
<211> LENGTH: 129
<212> TYPE: PRT
<213> ORGANISM: Bordetella bronchiseptica

<400> SEQUENCE: 32

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
        35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65              70                  75                  80

Leu Ala His Thr Lys Val Leu Gly Gly Glu Ser Asp Ser Val Thr
                85                  90                  95

Phe Asp Val Ala Lys Leu Ala Ala Gly Asp Asp Tyr Thr Phe Phe Cys
            100                 105                 110

Ser Phe Pro Gly His Gly Ala Leu Met Lys Gly Thr Leu Lys Leu Val
        115                 120                 125

Asp

<210> SEQ ID NO 33
<211> LENGTH: 162
<212> TYPE: PRT
<213> ORGANISM: Chloroflexus aurantiacus

<400> SEQUENCE: 33

Met Lys Ile Thr Leu Arg Met Met Val Leu Ala Val Leu Thr Ala Met
1               5                   10                  15

Ala Met Val Leu Ala Ala Cys Gly Gly Gly Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65              70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Gly Thr Tyr Leu Tyr
    130                 135                 140

Ile Cys Thr Val Pro Gly His Tyr Pro Leu Met Gln Gly Lys Leu Val
145                 150                 155                 160

Val Asn

<210> SEQ ID NO 34
```

```
<211> LENGTH: 140
<212> TYPE: PRT
<213> ORGANISM: Chloroflexus aurantiacus

<400> SEQUENCE: 34

Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
50                  55                  60

Gly Asp Val Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
                100                 105                 110

Pro Ala Pro Gly Thr Tyr Leu Tyr Ile Cys Thr Phe Pro Gly His Tyr
            115                 120                 125

Leu Ala Gly Met Lys Gly Thr Leu Thr Val Thr Pro
        130                 135                 140

<210> SEQ ID NO 35
<211> LENGTH: 16
<212> TYPE: PRT
<213> ORGANISM: Artificial sequence
<220> FEATURE:
<223> OTHER INFORMATION: conserved sequence of cupredoxin entry domain
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 35

Asp Gly Xaa Xaa Xaa Xaa Xaa Asp Xaa Xaa Tyr Xaa Lys Xaa Xaa Asp
1               5                   10                  15

<210> SEQ ID NO 36
<211> LENGTH: 183
<212> TYPE: PRT
<213> ORGANISM: Neisseris gonorrhoeae

<400> SEQUENCE: 36

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Gly Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
```

```
                50                  55                  60
Ser Asn Asp Asn Met Gln Phe Asn Thr Lys Asp Ile Gln Val Ser Lys
 65                  70                  75                  80

Ala Cys Lys Glu Phe Thr Ile Thr Leu Lys His Thr Gly Thr Gln Pro
                 85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180

<210> SEQ ID NO 37
<211> LENGTH: 18
<212> TYPE: PRT
<213> ORGANISM: Pseudomonas aeruginosa

<400> SEQUENCE: 37

Leu Ser Thr Ala Ala Asp Met Gln Gly Val Val Thr Asp Gly Met Ala
  1               5                  10                  15

Ser Gly

<210> SEQ ID NO 38
<211> LENGTH: 33
<212> TYPE: PRT
<213> ORGANISM: Chloroflexus aurantiacus

<400> SEQUENCE: 38

His Asn Trp Val Leu Val Asn Gly Gly Asp Asp Val Ala Ala Ala Val
  1               5                  10                  15

Asn Thr Ala Ala Gln Asn Asn Ala Asp Ala Leu Phe Val Pro Pro Pro
             20                  25                  30

Asp

<210> SEQ ID NO 39
<211> LENGTH: 28
<212> TYPE: PRT
<213> ORGANISM: Bordetella pertussis

<400> SEQUENCE: 39

Leu Thr Lys Thr Ala Asp Met Gln Ala Val Gl

```
Ala Ala Asp Thr Asp Tyr Val Lys Pro Asp Asp
            20                  25
```

<210> SEQ ID NO 41
<211> LENGTH: 21
<212> TYPE: PRT
<213> ORGANISM: Pseudomonas aeruginosa

<400> SEQUENCE: 41

```
Glu Ala Ala Asp Met Gln Gly Val Val Thr Asp Gly Met Ala Ser Gly
1               5                   10                  15

Leu Asp Lys Asp Tyr
            20
```

<210> SEQ ID NO 42
<211> LENGTH: 15
<212> TYPE: PRT
<213> ORGANISM: Pseudomonas aeruginosa

<400> SEQUENCE: 42

```
Glu Ala Ala Asp Met Gln Gly Val Val Thr Asp Gly Met Ala Ser
1               5                   10                  15
```

<210> SEQ ID NO 43
<211> LENGTH: 129
<212> TYPE: PRT
<213> ORGANISM: Bordetella pertussis

<400> SEQUENCE: 43

```
Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr

```
<213> ORGANISM: Pseudomonas syringae

<400> SEQUENCE: 45

Ser Lys Lys Ala Asp Ala Ser Ala Ile Thr Thr Asp G

4. The method of claim 1, wherein the cargo compound is an ultrasound contrast, agent and the location of the cargo compound is detected by ultrasound imaging.

5. A method for diagnosing cancer, comprising:
  contacting a cell with a complex comprising a cargo compound that comprises a detectable substance, said cargo compound linked to a peptide that consists of a sequence that is a truncation of a full-length wild-type cupredoxin or a H.8 outer membrane protein, wherein the peptide facilitates entry of the cargo compound into a mammalian cancer cell; and
  detecting the location of the cargo compound.

* * * * *